(12) United States Patent
Sugiyama et al.

(10) Patent No.: US 7,173,111 B2
(45) Date of Patent: Feb. 6, 2007

(54) WT1-INTERACTING PROTEIN WTIP

(75) Inventors: Haruo Sugiyama, 2-19-30, Senbanishi, Mino-shi, Osaka, 562-0036 (JP); Eui Ho Kim, Osaka (JP)

(73) Assignee: Haruo Sugiyama, Osaka (JP)

( * ) Notice: Subject to any disclaimer, the term of this patent is extended or adjusted under 35 U.S.C. 154(b) by 425 days.

(21) Appl. No.: 10/181,804

(22) PCT Filed: Jan. 24, 2001

(86) PCT No.: PCT/JP01/00461

§ 371 (c)(1),
(2), (4) Date: Jul. 23, 2002

(87) PCT Pub. No.: WO01/53484

PCT Pub. Date: Jul. 26, 2001

(65) Prior Publication Data

US 2003/0162220 A1    Aug. 28, 2003

(30) Foreign Application Priority Data

Jan. 24, 2000    (JP) ............................ 2000-014949

(51) Int. Cl.
*C07K 14/00*    (2006.01)
*C12P 21/06*    (2006.01)

(52) U.S. Cl. ..................................... 530/350; 435/69.1

(58) Field of Classification Search ................. None
See application file for complete search history.

(56) References Cited

FOREIGN PATENT DOCUMENTS

WO    WO 99/04265    1/1999

OTHER PUBLICATIONS

Bedford et al. FBP WW domains and the Abl SH3 domain bind to a specific class of a proline-rich ligands. The EMBO J (1997) vol. 16 (9), pp. 2376-2383.*
Faber et al., "Hunting Interacts with a Family of WW Domain Proteins," Hum. Mol. Genet., vol. 7, No. 9, (1998), pp. 1463-1467.
Chan et al., "Forming Binding Proteins Bear WWP/WW Domains that Bind Proline-Rich Peptides and Functionally Resemble SH3 Domains," EMBO J, vol. 15, No. 5, (1996), pp. 1045-1054.
Scanlan, "Antigens Recognized by Autologous Antibody in Patients with Renal-Cell Carcinoma," Int. J. Cancer., vol. 83, (1999), pp. 456-464.
Inoue, "WT1 As a New Prognostic Factor and a New Marker for the Detection of Minimal Residual Disease in Acute Leukemia," Blood, vol. 84, No. 9, (1994), pp. 3071-3079.
Bedford et al., "Formin Binding Protein 11," Database Swissprot 'Online, EBI, Hinxton, Cambridgeshire, U.K., Database Accession No. Q9R1C7, May 1, 2000, Abstract, XP-002237460.
Faber et al., "Huntingtin-Interacting Protein HYPA/FBP11 (Fragment)," Database Swissprot, 'Online, EBI, Hinxton, Cambridgeshire, U.K., Database Accession No. 075404, Nov. 1, 1998, Abstract, XP-002237461.
Hachiya et al., "Fas-Ligand Associated Factor 1 (Fragment)," Database Swissprot 'Online, EBI, Hinxton, Cambridgeshire, U.K., Database Accession No. 043856, Jun. 1, 1998, Abstract, XP-002237462.
Faber et al., "*Homo sapiens* Huntingtin-Interacting Protein HYPA/FBP11 (HYPA) mRNA, Partial cds," Database Swissprot 'Online, EBI, Hinxton, Cambridgeshire, U.K., Database Accession No. AF049528, Jul. 27, 1998, Abstract, XP-002237463.
"*Homo sapiens* cDNA Clone Similar to WP:ZK1098.1 CE03847; Contains Element TAR1 Repetitive Element; mRNA Sequence," National Cancer Institute, Database Accession No. AA902780, Apr. 9, 1998, Abstract, XP-002237464.
Scanlan et al., "NY-REN-6 Antigen (Fragment)," Database Swissprot 'Online, EBI, Hinxton, Cambridgeshire, U.K., Database Accession No. Q9Y5A8, Nov. 1, 1999, Abstract, XP-002237465.
Scanlan et al., "*Homo sapiens* NY-REN-6 Antigen mRNA, Partial cds," Database Swissprot 'Online, EBI, Hinxton, Cambridgeshire, U.K., Database Accession No. AF155096, Jul. 6, 1999, Abstract, XP-002237466.
Chew et al., "Renal Cancer Associated Antigen Precursor Sequence," Database Swissprot 'Online, EBI, Hinxton, Cambridgeshire, U.K., Database Accession No. AAYO7O53, Jul. 2, 1999, Abstract, XP-002237467.
Bedford et al., "*Mus musculus* Formin Binding Protein 11 (FBP) mRNA, Complete cds," Database Swissprot 'Online, EBI, Hinxton, Cambridgeshire, U.K., Database Accession No. AF135439, Jun. 21, 1999, Abstract, XP-002237468.

* cited by examiner

*Primary Examiner*—Remy Yucel
*Assistant Examiner*—Tara L. Garvey
(74) *Attorney, Agent, or Firm*—Foley & Lardner LLP

(57) ABSTRACT

An isolated WT1 interacting protein having the amino acid sequence as set forth in SEQ ID NO: 2, or an isolated protein that has an amino acid sequence in which one or a plurality of amino acids have been substituted, deleted, inserted, and/or added is functionally equivalent to the protein having the amino acid sequence as set forth in SEQ ID NO: 2; and comprises the amino acid sequence from Glu at position 449 to Met at position 541 in SEQ ID NO: 2.

5 Claims, 6 Drawing Sheets

Fig. 1
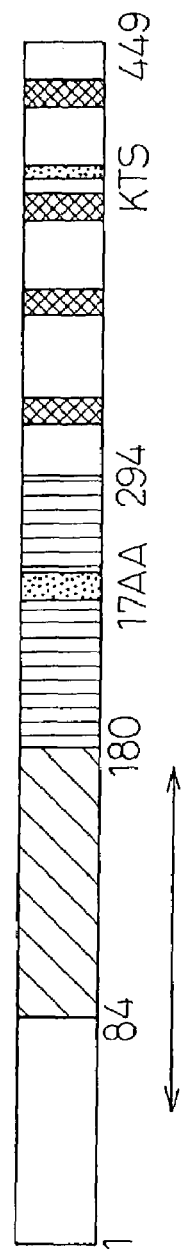
A
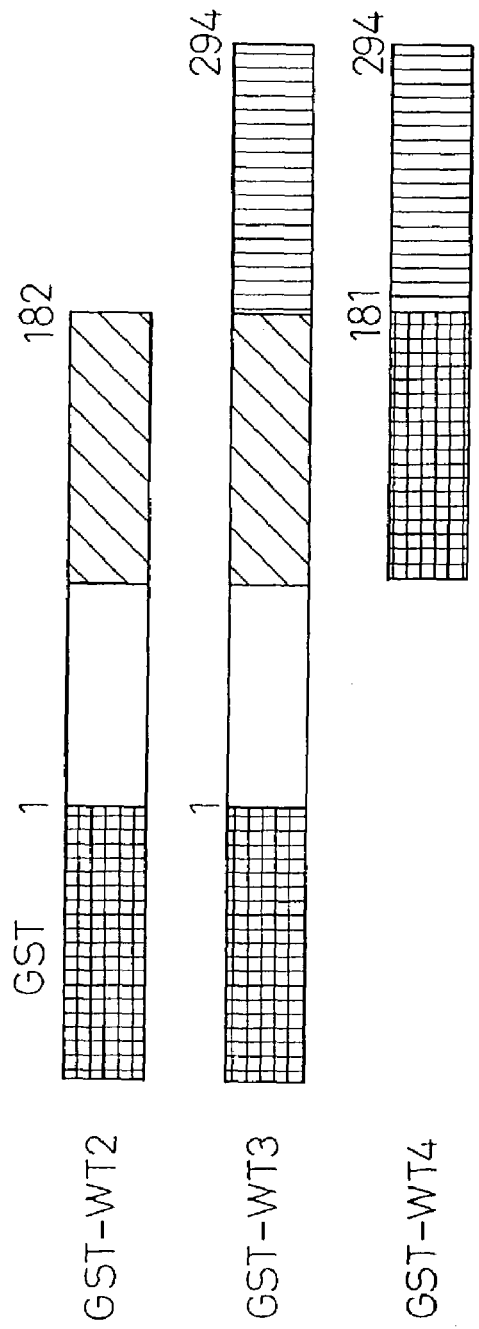
B

WT1-INTERACTING PROTEIN WTIP

This application is a 371 of PCT/JP01/00461 filed on Jan. 24, 2001 and claims benefit of JAPAN 2000-014949 filed on Jan. 24, 2000.

FIELD OF THE INVENTION

The present invention relates to a protein (WT1 interacting protein) (WTIP) that interacts with the WT1 protein, a gene encoding the same, and uses thereof.

BACKGROUND ART

WT1 (Wilms' tumor gene 1) gene is a transcription regulatory factor (Call K. M. et al., Cell 60, 509–520, 1990; Gessler M. et al., Nature 343, 774–778, 1990) discovered in the course of identifying a causative gene of Wilms' tumor which is a pediatric kidney tumor, and functions as a tumor suppressor gene in at least some Wilms' tumors. It was also discovered that its level of expression is high in most leukemia cells, and it is becoming clear that its level of expression at the first medical examination for leukemia correlates well with prognosis, and it is extremely useful as a marker of minimal residual disease (MRD) of leukemia (Inoue K. et al., Blood 84, 3071–3079, 1994).

In normal tissue, WT1 is highly expressed in the testis, the ovary, the spleen, the mesenchymal mesothelium as well as in the embryonal kidney. Among malignant tumors, it is also highly expressed in leukemia, malignant mesothelioma, and solid tumors such as lung cancer. There is increasing evidence that the WT1 gene is a gene having a variety of functions in organogenesis, oncogenesis and the like (Reddy J. C. et al., Biochim. Biophys. Acta. 1287, 1–28, 1996; Davices R. et al., Cancer Res. 59, 1747–1751, 1999).

The WT1 gene is mainly translated into four proteins by alternative splicing in the exons (A in FIG. 1). The longest gene product, in which exon 5 comprising 17 amino acid residues (17AA) and three amino acid residues (KTS[1]) in between the third and the fourth Zinc fingers have been inserted, is designated herein as WT1(+/+).

It has been demonstrated that the KTS-containing WT1 (+/+) has a weak DNA binding ability and binds to the mRNA splicing protein, whereas the WT1(+/−) having a potent DNA-binding ability functions as a transcription regulatory factor.

The WT1 protein is roughly composed of two regions, i.e., the function regulatory region and the DNA-binding region containing zinc fingers. In the function regulatory region, as shown in A in FIG. 1, have two domains that suppress or activate transcription. The assumption that proteins that bind to these regions may be responsible for the regulation of functions led to the discovery of various WT1 interacting proteins. They include various proteins such as p53 (Malheswran S. et al., Proc. Natl. Acad. Sci. USA 90, 5100–5104, 1993), ubiquitine conjugating enzyme 9 (Wany Z. Y. et al., J. Biol. Chem. 271, 24811–24816, 1996), par-4 (Johnstone R. W. et al., Mol. Cell Biol. 16, 6945–6956, 1990), U2AF65 (Ravis R. C. et al., Geves. Rev. 12, 3217–3225, 1998), and hsp70 (Maheswaran S. et al., Geves Rev. 12, 1108–1120, 1998). However, there are no reports of specific binding proteins in leukemia cells.

DISCLOSURE OF THE INVENTION

Thus, it is an object of the present invention to provide a novel protein that interacts with (binds to) the WT1 protein, a gene encoding it, uses thereof and the like.

Thus, the present invention provides (1) a WT1 interacting protein having the amino acid sequence as set forth in SEQ ID NO: 2, or a protein that has an amino acid sequence in which one or a plurality of amino acids have been substituted, deleted, inserted, and/or added in the amino acids of said protein and that is functionally equivalent to the protein having the amino acid sequence as set forth in SEQ ID NO: 2.

The present invention also provides (2) a protein that is encoded by DNA hybridizing under a stringent condition to DNA having the nucleotide sequence as set forth in SEQ ID NO: 1 and that is functionally equivalent to the protein having the amino acid sequence as set forth in SEQ ID NO: 2.

The present invention also provides (3) a WT1 interacting protein comprising an amino acid sequence from positions 449 to 541 in SEQ ID NO: 2.

The present invention also provides (4) a function modulator of the WT1 protein comprising, as an active ingredient, a polypeptide comprising an amino acid sequence from Glu at position 449 to Met at position 541 in SEQ ID NO: 2.

The present invention also provides (5) a partial peptide of the protein described in the above (1) or (2).

The present invention also provides (6) a gene encoding a protein described in any of the above (1) to (3).

The present invention also provides (7) a vector comprising the gene described in the above (6).

The present invention also provides (8) a host cell carrying the vector described in the above (7).

The present invention also provides (9) a method of producing a protein described in any of the above (1) to (3), said method comprising culturing the host cell of the above (8).

The present invention also provides (10) an antibody to a protein described in any of the above (1) to (3).

The present invention also provides (11) a method of detecting or determining a protein described in any of the above (1) to (3) comprising:

(a) bringing the antibody described in the above (10) into contact with a sample expected to contain said protein; and (b) detecting or determining the formation of an immune complex between said antibody and said protein or immunostaining the cells that express said protein using said antibody.

The present invention also provides (12) DNA that specifically hybridizes to DNA comprising the base sequence as set forth in SEQ ID NO: 1 and that has a chain length of at least 15 bases.

The present invention also provides (13) a method of screening a compound that binds to a protein described in any of the above (1) to (3), said method comprising the steps of:

(a) bringing a sample to be tested into contact with said protein or a partial peptide thereof;

(b) detecting the binding activity of said sample with said protein or a partial peptide thereof; and (c) selecting a compound having an activity of binding to said protein or a partial peptide thereof.

The present invention also provides (14) a compound that can be isolated by the method described in the above (13) and that binds to a protein described in any of the above (1) to (3).

The present invention also provides (15) a method of screening a compound that promotes or inhibits the activity of a protein described in any of the above (1) to (3), said method comprising the steps of:

(a) culturing the cells that express said protein in the presence of a sample to be tested;
(b) detecting the growth of said cells; and
(c) selecting a compound that promotes or inhibits said growth as compared to when detected in the absence of said sample to be tested.

The present invention also provides (16) a compound that can be isolated by the method described in the above (15) and that promotes or inhibits the activity of a protein described in any of the above (1) to (3).

The present invention also provides (17) a method of screening a compound that promotes or inhibits the binding of the WT1 interacting protein described in any of the above (1) to (3) with the WT1 protein, said method comprising the steps of:
(a) allowing the WT1 interacting protein to react with the WT1 protein in the presence of a sample to be tested;
(b) determining the binding activity of both proteins; and
(c) selecting a compound that promotes or inhibits said binding as compared to when detected in the absence of said sample to be tested.

The present invention also provides (18) a compound that can be isolated by the method described in the above (17) and that promotes or inhibits the binding of the WT1 interacting protein described in any of the above (1) to (3) with the WT1 protein.

BRIEF EXPLANATION OF THE DRAWINGS

In FIG. 1, A is a drawing that shows the structure of cDNA encoding the full-length of the WT1 protein, whereas B is a drawing that shows the structure of a fusion protein (GST-WT2) of the suppressive domain of the WT1 protein and GST (glutathione S-transferase) and a fusion protein (GST-WT3) of the suppressive domain and the activating domain and GST, and a fusion protein (GST-WT4) of the activating domain and GST.

EMBODIMENTS FOR CARRYING OUT THE INVENTION

Figure 2:
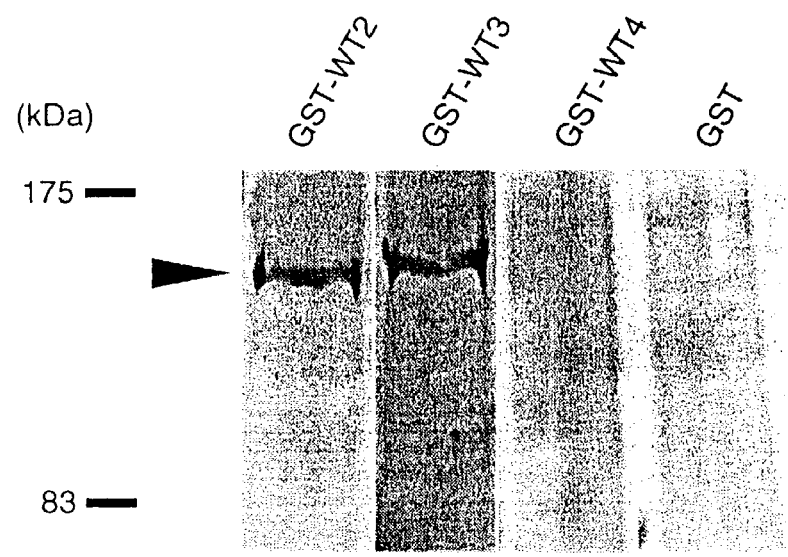
FIG. 2 is an electrophoretogram that shows the reactivity of the extracts of the K562 cells with the fusion protein shown in B of FIG. 1 and with GST alone. It shows that there is an about 115 kDa protein present in the extract of the K562 cells, that binds to the suppressive domain of the WT1 protein.

In order to obtain a novel protein that binds to the WT1 protein, WT1 interacting proteins were searched for using a human leukemia cell line K562 (Yamagami T. et al., Blood 87,2878–2885, 1996) in which growth inhibition is observed when using an antisense oligo DNA of WT1. In a west western blot using a fusion protein of the WT1 regulatory region and glutathione S-transferase (GST), an intracellular protein that binds to the fusion protein was noted, which thereby was separated by a column chromatography and SDS-PAGE, and a gene was identified by peptide mapping and by screening with expression. As a result, cDNA of a novel gene WT1 interacting protein (WTIP) was cloned.

Thus the present invention provides a WT1 interacting protein having the amino acid sequence as set forth in SEQ ID NO: 1.

In the sequence described in SEQ ID NO: 1, the nucleotide sequence of positions 1 to 1358 corresponds to FBP11 (Chan D. C. et al., EMBO J. 15, 1045–1054, 1996) which is one of the proteins (formin binding protein) binding to formin involved in the development of mouse legs and kidney and HYPA (Huntington yeast partner A) (Faber P. W. et al., Hum. Mol. Genet. 7, 1463–1467, 1998) which is one of the proteins binding to Huntington that is considered to be a causative gene of Huntington's chorea, a human neurodegenerative disease, and the amino acid sequence corresponding to the nucleotide sequence of positions 1636 to 2980 in SEQ ID NO: 1 corresponds to NY-REN-6 (Scanlan M. J. et al., Int. J. Cancer 83, 456–464, 1999) identified as an autoantigen that recognizes an autoantibody in the serum of human patients with kidney cancer.

Thus, a protein having a full-length and partial amino acid sequence, comprising the amino acid sequence corresponding to the nucleotide sequence of positions 1359 to 1635 in SEQ ID NO: 1, is novel. Thus, the present invention provides a protein comprising an amino acid sequence that corresponds to the nucleotide sequence of positions 1359 to 1635 in SEQ ID NO: 1.

The present invention also provides a gene, for example DNA or RNA, encoding the above protein. Said DNA is specifically cDNA.

The present invention also provides a vector comprising the above DNA, for example an expression vector.

In accordance with the present invention, it was found that the WW domain from Gly at position 141 to Asp at position 217 in SEQ ID NO: 2 is a binding region with the WT1 protein. Thus the present invention provides a regulatory agent of WT1 protein function comprising, as an active ingredient, a polypeptide comprising an amino acid sequence from Gly at position 141 to Asp at position 217 in SEQ ID NO: 2. In accordance with the present invention, a polypeptide having an amino acid sequence of position 1 (Met) to position 98 (Gly) in SEQ ID NO: 2 does not bind to the WT1 protein, but a polypeptide having an amino acid sequence of position 1 (Met) to position 178 (Ala) binds to the WT1 protein. Thus, according to one aspect of the present invention, there is provided a regulatory agent of WT1 protein function comprising as an active ingredient a polypeptide having or comprising an amino acid sequence from position 99 (Gln) to position 178 (Ala) in SEQ ID NO: 2.

In accordance with the present invention, a polypeptide having an amino acid sequence of position 1 (Met) to position 406 (Glu) in SEQ ID NO: 2 binds to the WT1 protein. Thus, according to one aspect of the present invention, there is provided a regulatory agent of WT1 protein function comprising, as an active ingredient, a polypeptide having or comprising an amino acid sequence from position 99 (Gln) to position 406 (Glu) in SEQ ID NO: 2. More generally, the present invention provides a regulatory agent of WT1 protein function comprising, as an active ingredient, a polypeptide or a protein from any amino acid of position 1 (Met) to position 99 (Gln) to any amino acid of position 189 (Glu) to position 406 (Glu) or position 957 (Gin) in SEQ ID NO: 2.

The isolation of WTIP and the cloning of cDNA encoding it is described in Example 1. In the example, human leukemia cell-like K562 (Japanese Cancer Research Resource Banks) was used as a source for isolating WTIP and DNA encoding it, but other cells that produce WTIP may also be used.

The present invention encompasses proteins functionally equivalent to the WT1 interacting protein. Such proteins include homolog proteins of other organisms corresponding to the human WT1 interacting protein and mutants of the human WT1 interacting protein. As used herein the term "functionally equivalent" means that the subject protein has a biological activity equivalent to the above WT1 interacting protein. The biological activity is, for example, a binding activity with the WT1 protein.

As a method well known to a person skilled in the art for preparing a protein functionally equivalent to a certain protein, there is known a method of introducing mutation in the protein. For example, a person skilled in the art can use site-directed mutagenesis (Hashimoto-Gotoh, T. et al. (1995) Gene 152, 271–275; Zoller, M. J. and Smith, M. (1983) Methods Enzymol. 100, 468–500; Kramer, W. et al. (1984) Nucleic Acids Res. 12, 9441–9456; Kramer W. and Fritz H. J. (1987) Methods Enzymol. 154, 350–367; Kunkel, T. A. (1985) Proc. Natl. Acad. Sci. USA 82, 488–492; Kunkel (1988) Methods Enzymol. 85, 2763–2766) to introduce as appropriate a mutation in amino acids of the human WT1 interacting protein in order to prepare a protein functionally equivalent to the human WT1 interacting protein.

Mutation in amino acids also occurs spontaneously in nature. Thus, proteins that have an amino acid sequence in which one or a plurality of amino acids are mutated in the amino acid sequence of the human WT1 interacting protein and that are functionally equivalent the human WT1 interacting protein are also encompassed in the present invention.

As proteins functionally equivalent to the WT1 interacting protein of the present invention, there can be specifically mentioned those in which one or more than one, preferably two or more and 30 or less, more preferably two or more and 10 or less amino acids have been deleted in the amino acid sequence as set forth in SEQ ID NO: 2, those in which one or more than one, preferably two or more and 30 or less, more preferably two or more and 10 or less amino acids have been added in the amino acid sequence as set forth in SEQ ID NO: 2, and those in which one or more than one, preferably two or more and 30 or less, more preferably two or more and 10 or less amino acids have been substituted with other amino acids in the amino acid sequence as set forth in SEQ ID NO: 2.

For the amino acid residue that is mutated, it is preferably mutated to another amino acid that retains the property of the amino acid side chain. For example, as the properties of amino acid side chains, there may be mentioned hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxy group-containing side chain (S, T, Y), amino acids having a sulfur-containing side chain (C, M), amino acids having a carboxylic acid- or amide-containing side chain (D, N, E, Q), amino acids having a base-containing side chain (R, K, H), and amino acids having an aromatic-containing side chain (H, F, Y, W) (all letters in parentheses indicate a one-letter representation of amino acids).

It is already known that proteins having an amino acid sequence that has been modified by deletion, addition of one or a plurality of amino acid residues and/or substitution with another amino acid in a certain amino acid sequence can retain the biological activity (Mark, D. F. et al., Proc. Natl. Acad. Sci. USA (1984) 81, 5662–5666; Zoller, M. J. & Smith, M., Nucleic Acids Research (1982) 10, 6487–6500; Wang, A. et al., Science 224, 1431–1433; Dalbadie-McFarland, G. et al., Proc. Natl. Acad. Sci. USA (1982) 79, 6409–6413).

As a protein in which one or a plurality of amino acids have been added to the amino acid sequence (SEQ ID NO: 2) of the human WT1 interacting protein, there can be mentioned a fusion protein that contains the human WT1 interacting protein. A fusion protein is a fusion of the human WT1 interacting protein and another peptide or protein, and is included in the present invention. In a method of creating a fusion protein, DNA encoding the human WT1 interacting protein of the present invention and DNA encoding another peptide or protein are linked in a frame with each other, which is then introduced into an expression vector and expressed in a host cell, and a method well known to a person skilled in the art can be used. Any other peptide or protein that is subjected to fusion with the protein of the present invention is not specifically limited.

As another peptide that is subjected to fusion with the protein of the present invention, for example, known peptides may be used including FLAG (Hopp, T. P. et al., BioTechnology (1988) 6, 1204–1210), 6×His (SEQ ID NO: 13) comprising 6 His (histidine) (SEQ ID NO: 13) residues, 10×His (SEQ ID NO: 14), influenza hemagglutinin (HA), fragments of human c-myc, fragments of VSV-GP, fragments of p18HIV, T7-tag, HSV-tag, E-tag, fragments of SV40T antigen, lck tag, fragments of α-tubulin, B-tag, fragments of Protein C, and the like. As another protein that is subjected to fusion with the protein of the present invention, there may be mentioned, for example, GST (glutathione S-transferase), HA (influenza agglutinin), the constant regions of immunoglobulin, β-galactosidase, MBP (maltose-binding protein), and the like.

DNA encoding such a peptide or protein is fused to DNA encoding the protein of the present invention, and the fused DNA thus prepared is expressed to prepare the fusion protein.

As a method well known to a person skilled in the art for preparing a protein functionally equivalent to a certain protein, there can be mentioned a method that employs the hybridization technology (Sambrook, J. et al., Molecular Cloning 2nd ed., 9.47–9.58, Cold Spring Harbor Laboratory Press, 1989).

Thus, it can be routinely performed by a person skilled in the art that a DNA sequence (SEQ ID NO: 1) encoding the human WT1 interacting protein or a portion thereof is used to isolate DNA having a high homology therewith, and from said DNA a protein functionally equivalent to the human WT1 interacting protein can be routinely isolated. Thus, a protein encoded by DNA that hybridizes to DNA encoding the human WT1 interacting protein or DNA comprising a portion thereof and that is functionally equivalent to the human WT1 interacting protein is also included in the present invention.

As such a protein, there can be mentioned a homolog from a mammal other than the human (for example, a protein encoded by a monkey, mouse, rat, rabbit, and bovine gene). When a cDNA having a high homology with DNA encoding the human WT1 interacting protein is isolated from an animal, preferably tissues such as the heart, the placenta, the testis and the like are used.

A hybridization condition for isolating a DNA encoding a protein functionally equivalent to the human WT1 interacting protein may be selected, as appropriate, by a person skilled in the art. As the hybridization condition, there can be mentioned a low stringent condition. A low stringent condition is, for example, 42° C., 2×SSC, and 0.1% SDS, and preferably 50° C., 2×SSC, and 0.1% SDS.

More preferably, there can be mentioned a high stringent condition. As a high stringent condition, for example, there can be mentioned 65° C., 2×SSC, and 0.1% SDS. In these conditions, the higher the temperature is the higher the homology of the DNA obtained is. However, as elements affecting the stringency of hybridization, a plurality of elements can be conceived such as a salt concentration in addition to temperature, and a person skilled in the art can select, as appropriate, these elements to attain a similar stringency.

Isolation can also be attained by utilizing a gene amplifying method using primers synthesized based on the sequence information of DNA (SEQ ID NO: 1) encoding the human WT1 interacting protein, for example a polymerase chain reaction (PCR), in place of hybridization.

A protein functionally equivalent to the human WT1 interacting protein encoded by the DNA isolated by such a hybridization technology or gene amplification technology usually has a high homology with the human WT1 interacting protein in terms of the amino acid sequence.

The protein of the present invention also includes a protein that is functionally equivalent to the human WT1 interacting protein and that has a high homology with the amino acid sequence as set forth in SEQ ID NO: 2. A high homology as used herein means a homology of 70% or higher, preferably 80% or higher, more preferably 90% or higher, and more preferably 95% or higher in identity. In order to determine the homology of proteins, an algorithm described in an article (Wilbur, W. J. and Lipman, D. J., Proc. Natl. Acad. Sci. USA (1983) 80, 726–730) may be used.

The protein of the present invention may differ in amino acid sequence, molecular weight, isoelectric point, or the presence or absence and shapes of sugar chains depending on the cells, described below, that produce it, the host cells, and the method of purification. However, it is included in the present invention as long as the protein obtained retains functions equivalent to the human WT1 interacting protein of the present invention (SEQ ID NO: 2). For example, when the protein of the present invention is expressed in prokaryotic cells such as Escherichia coli (E. coli), a methionine residue is added to the N-terminal of the amino acid sequence of the original protein. Also, when it is expressed in eukaryotic cells such as mammalian cells, the signal sequence at the N-terminal is removed. The protein of the present invention encompasses such proteins.

The protein of the present invention can be prepared by a person skilled in the art in a known method either recombinantly or as natural protein. In the case of recombinant proteins, DNA (such as DNA having the base sequence as set forth in SEQ ID NO: 1) encoding a protein of the present invention is integrated into a suitable expression vector, which in turn is introduced into a suitable host cell and a recombinant is recovered therefrom to obtain an extract. Then the extract is purified by subjecting it to ion exchange, reverse-phase, gel filtration chromatography, or affinity chromatography in which an antibody against the protein of the present invention has been immobilized on the column, or by using a combination of a plurality of columns to prepare the protein of the present invention.

When the protein of the present invention was expressed as a fusion protein with the glutathione S-transferase protein or as a recombinant protein to which a plurality of histidines were added in a host cell (for example, in an animal cell or E. coli), the expressed recombinant protein can be purified by a glutathione column or a nickel column.

After purification of the fusion protein, the regions other than the protein of interest among the fusion protein may be removed, as desired, by cleaving with thrombin, Factor Xa etc.

In the case of a natural protein, it can be purified and isolated by subjecting an extract of a tissue or cell that expresses the protein of the present invention it to an affinity column to which an antibody, described below, that binds to the WT1 interacting protein is bound. The antibody may be a polyclonal antibody or a monoclonal antibody.

The present invention also encompasses the partial peptides of the protein of the present invention. The partial peptides comprising the amino acid sequence specific to the protein of the present invention comprises at least 7 amino acids, preferably 8 amino acids or more, and more preferably 9 amino acids or more. Said partial peptides can be used for preparing an antibody against the protein of the present invention, screening compounds that bind to the protein of the present invention, and screening promoters and inhibitors of the protein of the present invention. Furthermore, they can be an antagonist to ligands of the protein of the present invention.

As the partial peptides of the present invention, for example, there can be mentioned partial peptides comprising an active center of the protein comprising the amino acid sequence as set forth in SEQ ID NO: 2. There can also be mentioned partial peptides containing one or a plurality of regions of the hydrophobic regions and hydrophilic regions deduced from the hydrophobicity plot analysis. These partial peptides may contain part or all of a hydrophobic region, or contain part or all of a hydrophilic region.

The partial peptide of the present invention can be produced by gene engineering technology, known peptide synthetic methods, or by cleaving the protein of the present invention with a suitable peptidase. As the peptide synthesis method, any of a solid-phase synthesis and a liquid-phase synthesis can be used.

The present invention also relates to DNA encoding the protein of the present invention. The DNA of the present invention can be used for the in vivo or in vitro production of the protein of the present invention and, besides, the application in gene therapy to diseases associated with aberrations in the gene encoding the protein of the present invention is contemplated.

The DNA of the present invention may be in any form as long as it can encode the protein of the present invention. Thus, it can be any of cDNA synthesized from mRNA, genomic DNA, or chemically synthesized DNA. Furthermore, it contains DNA having any base sequence based on the degeneracy of genetic code, as long as it encodes the protein of the present invention.

The DNA of the present invention can be prepared by any method known to a person skilled in the art. For example, it can be prepared by preparing a cDNA library from the cells expressing the protein of the present invention and subjecting it to hybridization using, as the probe, part of the DNA sequence (for example SEQ ID NO: 1) of the present invention. cDNA libraries may be prepared by a method described in Sambrook, J. et al., Molecular Cloning, Cold Spring Harbor Laboratory Press (1989), or commercially available DNA libraries may be used. It is also possible to prepare RNA from the cells expressing the protein of the present invention, synthesizing an oligo DNA based on the DNA sequence (for example SEQ ID NO: 1) of the present invention, which is then used as a primer in a PCR reaction to amplify cDNA encoding the protein of the present invention.

By determining the nucleotide sequence of the cDNA obtained, the translation region encoding it can be determined, and thereby the amino acid sequence of the protein of the present invention can be obtained. Furthermore, genomic DNA can be isolated by screening a genomic DNA library using the obtained cDNA as the probe.

Specifically the following method can be followed. First, mRNA is isolated from cells, tissues, or organs (for example, the ovary, the testis, the placenta etc.) expressing the protein of the present invention. The isolation of mRNA can be effected by preparing total RNA using a known method such as the guanidine ultracentrifugation method (Chirgwin, J. M. et al., Biochemistry (1979) 18, 5294–5299), the AGPC method (Chomczynski, P. and Sacchi, N., Anal. Biochem. (1987) 162, 156–159) and the like, and then by purifying mRNA from total RNA using the mRNA Purification Kit (Pharmacia) and the like. mRNA can also be prepared directly by using the QuickPrep mRNA Purification Kit (Pharmacia).

cDNA is synthesized from the mRNA obtained using a reverse transcriptase. The synthesis of cDNA can be effected using the AMV Reverse Transcriptase First-Strand cDNA Synthesis Kit (Seikagaku Kogyo), and the like. Alternatively, for the synthesis and amplification of cDNA, the 5'-Ampli FINDER RACE kit (manufactured by Clontech) and the 5'-RACE method (Frohman, M. A. et al., Proc. Natl. Acad. Sci. U.S.A. (1988) 85, 8998–9002; Belyavsky, A. et al., Nucleic Acids Res. (1989) 17, 2919–2932), that employs the polymerase chain reaction (PCR), may be used.

A DNA fragment of interest may be prepared from the PCR product thus obtained and ligated to a vector DNA. Furthermore, a recombinant vector is constructed from this, which is then introduced into E. coli for selection of colonies to prepare the desired recombinant vector. The base sequence of the desired DNA may be confirmed by a known method such as the dideoxy nucleotide chain termination method.

Considering the frequency of use of the host's codon for use in the present invention, a sequence having a better efficiency of expression can be designed (Grantham, R. et al., Nucleic Acids Research (1981) 9, r43–r74). Furthermore, the DNA of the present invention may be altered by using commercially available kits or by known methods. Alternative includes, for example, digestion with a restriction enzyme, insertion of a synthetic oligonucleotide or a suitable DNA fragment, addition of a linker, insertion of an initiation codon (ATG) and/or a stop codon (ATT, TGA or TAG), and the like.

The DNA of the present invention includes DNA that hybridizes to the DNA comprising the base sequence as set forth in SEQ ID NO: 1 under a stringent condition and DNA that encodes a protein functionally equivalent to the above protein of the present invention.

As the stringent condition, which can be chosen as appropriate by a person skilled in the art, there can be mentioned a low stringent condition. A low stringent condition is, for example, 42° C., 2×SSC, and 0.1% SDS, and preferably 50° C., 2×SSC, and 0.1% SDS. More preferably, there can be mentioned a high stringent condition. As a high stringent condition, for example, there can be mentioned 65° C., 2×SSC, and 0.1% SDS. In these conditions, the higher the temperature is the higher the homology of DNA obtained is. The above hybridizing DNA may preferably be naturally occurring DNA, for example cDNA or chromosomal DNA.

The present invention also relates to a vector in which the DNA of the present invention has been inserted. The vector of the present invention is useful in retaining the DNA of the present invention in the host cell and in expressing the protein of the present invention.

The vector is not specifically limited, as long as it has "ori" for use in amplification in E. coli to produce and amplify in large quantities the vector in E. coli (for example, JM109, DH5α, HB101, XL1Blue) when E. coli is used as the host, and a selection gene (for example a drug resistance gene that can be identified by a drug such as ampicillin, tetracycline, kanamycin, and chloramphenicol) in the transformed E. coli.

Examples of vectors include M13 vectors, pUC vectors, pBR322, pBluescript, pCR-Script and the like. Also, for the purpose of subcloning and excising of DNA, pGEM-T, pDIRECT, pT7 etc., in addition to the above vector, may be mentioned. When a vector is used to produce the protein of the present invention specifically, the use of an expression vector is useful.

When expression is to be effected in E. coli, the expression vector should have the above characteristics so that it can be expressed in E. coli, and besides, when the host is such E. coli as JM109, DH5α, HB101, XL1-Blue etc., it must have a promoter that permits efficient expression in E. coli, such as the lacz promoter (Ward et al., Nature (1989) 341: 544–546; FASEB J. (1992) 6, 2422–2427), the ara B promoter (Better et al., Science (1988) 240, 1041–1043), the T7 promoter, or the like. As such vectors, there may be mentioned, in addition to the above vectors, pGEX-5X-1 (manufactured by Pharmacia), "QIAexpress system" (manufactured by Qiagen), pEGFP, pET (in this case, the host is preferably BL21 that is expressing T7 RNA polymerase), or the like.

The vector can also contain a signal sequence for polypeptide secretion. As the signal sequence for protein secretion, when produced in the periplasm of E. coli, the pelB signal sequence (Lei, S. P. et al., J. Bacteriol. (1987) 169, 4379) can be used. The introduction of a vector into the host cell may be effected by, for example, the calcium chloride method and the electroporation method.

For the production of the protein of the present invention, in addition to E. coli, there can be mentioned expression vectors derived from mammals (for example, pcDNA3 (manufactured by Invitrogen), pEGF-BOS (Nucleic Acids Res. 18 (17), 5322, 1990), pEF, pCDM8), expression vectors derived from insect cells (for example, "Bac-to-Bac baculovirus expression system" (manufactured by GIBCO BRL), pBacPAK8), expression vectors derived from plants (for example, pMH1, pMH2), expression vectors derived from animal viruses (for example, pHSV, pMV, pAdexLcw), expression vectors derived from retrovirus vectors (for example, pZIpneo), expression vectors derived from yeast (for example, "Pichia Expression Kit" (manufactured by Invitrogen), pNV11, SP-Q01), expression vectors derived from Bacillus subtilis (for example, pPL608, pKTH50), and the like.

For the purpose of expressing in animal cells such as CHO cells, COS cells, NIH3T3 cells and the like, it is indispensable for the vectors to have promoters required for expression in cells such as SV40 promoter (Mulligan et al., Nature (1979) 277, 108), MMLV-LTR promoter, EF1α promoter (Mizushima et al., Nucleic Acids Res. (1990) 18, 5322), CMV promoter and the like, and more preferably to have genes (such as a drug resistant gene that can be identified by a drug such as neomycin, G418) for selecting transformation into the cell. As vectors having such characteristics, there can be mentioned for example PMAM, pDR2, PBK-RSV, PBK-CMV, pOPRSV, pOP13 and the like.

Furthermore, for the purpose of stably expressing a gene and amplifying the copy number of a gene in the cell, there may be mentioned a method in which a vector (for example, pCHOI) having the DHFR gene is introduced into the CHO cells deficient in the nucleic acid synthetic pathway to complement the deficiency and is amplified with methotrexate (MTX). For the purpose of transient expression of a gene, there may be mentioned a method in which transformation is effected with a vector (pcD etc.) having the origin of replication for SV40 using COS cells having on the chromosome a gene that expresses the SV40 T antigen.

As the origin of replication, there can be used those derived from polyoma virus, adenovirus, bovine papilloma virus (BPV) and the like. Furthermore, for the amplification of gene copy numbers in the host cell system, expression vectors can include, as selectable markers, the aminoglycoside transferase (APH) gene, the thymidine kinase (TK) gene, E. coli xanthine guaninephosphoribosyl transferase (Ecogpt) gene, the dihydrofolate reductase (dhfr) gene and the like.

On the other hand, as methods of expressing the DNA of the present invention in an organism, there can be mentioned a method in which the DNA of the present invention is integrated into a suitable vector, and then introduced into an organism by the retrovirus method, the liposome method, the cationic liposome method, the adenovirus method and the like. This permits the gene therapy of diseases associated with mutation in the gene of the present invention. As the vector used, there can be mentioned, but not limited to, an adenovirus vector (for example, pAdexlcw), a retrovirus vector (for example, pZIPneo) and the like. Common genetic manipulation such as the insertion of the DNA of the present invention into a vector may be performed by a standard method (Molecular Cloning, 5.61–5.63). The administration into an organism may be an ex vivo method or an in vivo method.

The present invention also relates to a host cell into which the vector of the present invention has been introduced. The host cell into which the vector of the present invention is introduced is not specifically limited, and E. coli and various animal cells may be used. For example, the host cell of the present invention can be used for the production of the protein of the present invention or as a production system for expression. The production system of protein preparation comprises the in vitro and the in vivo production system. As an in vitro production system, there can be mentioned a production system which employs eukaryotic cells and a production system which employs prokaryotic cells.

When the eukaryotic cells are used, there are the production systems which employ the animal cells, the plant cells, and the fungal cells. Known animal cells include mammalian cells such as CHO cells (J. Exp. Med. (1995) 108, 945), COS cells, 3T3 cells, myeloma cells, baby hamster kidney (BHK) cells, HeLa cells and Vero cells, amphibian cells such as Xenopus oocytes (Valle, et al., Nature (1981) 291, 358–340), or insect cells such as sf9, sf21, and Tn5.

As the CHO cells, dhfr-CHO (Proc. Natl. Acad. Sci. U.S.A. (1968) 77, 4216–4220), a CHO cell that is deficient in the DHFR gene, and CHO K-1 (Proc. Natl. Acad. Sci. U.S.A. (1968) 60, 1275) can be preferably used. In animal cells, for the purpose of large scale production, CHO cells are specifically preferred. The introduction of a vector into the host cell may be carried out by, for example, the calcium phosphate method, the DEAE-dextran method, the cationic ribozome DOTAP (manufactured by Boehringer Mannheim), the electroporation method, and the lipofection method.

As plant cells, for example, there are known cells derived from Nicotiana tabacum as the protein production system, which may subjected to callus culture. Known fungal cells include yeasts such as the genus Saccharomyces, more specifically Saccharomyces cereviceae, or filamentous fungi such as the genus Aspergillus, more specifically Aspergillus niger.

When the prokaryotic cells are used, there are the production systems which employ bacterial cells. Known bacterial cells include Escherichia coli (E. coli) such as JM109, DH5α and HB101, and Bacillus subtilis.

By transforming these cells with the desired DNA and culturing the transformed cells in vitro, proteins can be obtained. Culturing is conducted using known methods. For example, as the culture liquid, DMEM, MEM, RPMI1640, and IMDM can be used, and hereupon serum supplements such as fetal calf serum (FCS) may be used in combination, or serum-free medium can be used. pH during the culture is preferably about 6 to 8. Culture is usually carried out at about 30 to 40° C. for about 15 to 200 hours with, as desired, medium change, aeration, and agitation.

On the other hand, as in vivo production systems, there can be mentioned those which employ animals and those which employ plants. The DNA of interest is introduced into these animals or plants, and the proteins are produced in the body of such animals or plants, and recovered. The term "host cell" as used herein encompasses these animals and plants.

When animals are used, there are the production systems which employ mammals and insects. As mammals, goats, pigs, sheep, mice, and cattle can be used (Vicki Glaser, SPECTRUM Biotechnology Applications, 1993). When mammals are used, transgenic animals can be used.

For example, the DNA of interest is prepared as a fusion gene with a gene encoding protein which is inherently produced in the milk such as goat β casein. The DNA fragment containing the fusion gene into which the DNA has been inserted is injected into a goat embryo, and the embryo is introduced into a female goat. The protein of interest can be obtained from the milk produced by the transgenic goat borne to the goat who received the embryo or the offspring thereof. In order to increase the amount of milk containing the protein produced by the transgenic goat, hormones may be given to the transgenic goat as appropriate. (Ebert, K. M. et al., Bio/Technology (1994) 12, 699–702).

As an insect, silkworms may be used. When silkworms are used, baculovirus into which the DNA of interest has been inserted is infected to the silkworm, and the desired protein can be obtained from the body fluid of the silkworm (Susumu, M. et al., Nature (1985) 315, 592–594).

Moreover, when plants are used, tabacco, for example, can be used. When tabacco is used, the DNA of interest is inserted into an expression vector for plants, for example pMON 530, and then the vector is introduced into a bacterium such as *Agrobacterium tumefaciens*. The bacterium is then infected to tabacco such as *Nicotiana tabacum* to obtain the desired protein from the leaves of the tabacco (Julian, K. -C. Ma et al., Eur. J. Immunol. (1994) 24, 131–138)

Proteins of the present invention thus obtained can be separated from the inside or outside (culture medium etc.) of the host cell and then may be purified as virtually pure and homogeneous proteins. Separation and purification of the antibody for use in the present invention may be accomplished by, but not limited to, separation and the purification methods conventionally used for protein purification. Proteins can be separated and purified by selecting and combining, as appropriate, methods including chromatography columns, filtration, ultrafiltration, salting-out, solvent precipitation, distillation, immunoprecipitation, SDS-polyacrylamide gel electrophoresis, isoelectric focusing, dialysis, recrystallization and the like.

As chromatography, there may be mentioned, for example, affinity chromatography, ion exchange chromatography, hydrophobic chromatography, gel-filtration, reverse phase chromatography, adsorption chromatography, and the like (Strategies for Protein Purification and Characterization: A Laboratory Course Manual. Ed Daniel R. Marshak et al., Cold Spring Harbor Laboratory Press, 1996). These chromatographies can be carried out using a liquid chromatography such as HPLC and FPLC. The present invention encompasses proteins that were highly purified using these purification methods.

Furthermore, before or after purification, proteins can be modified or peptides can be partially removed as appropriate by acting a suitable protein modifying enzyme. As the protein modifying enzyme, there can be used, for example, trypsin, chymotrypsin, lysyl endopeptidase, protein kinase, and glucosidase.

The present invention also relates to antibody that binds to the protein of the present invention. The form of the protein of the present invention is not specifically limited, and includes polyclonal antibody as well as monoclonal antibody. Furthermore, antiserum obtained by immunizing an immune animal such as a rabbit with the protein of the present invention, all classes of polyclonal antibodies and monoclonal antibodies, and moreover human antibodies and humanized antibodies by gene recombinant technology.

Though the protein of the present invention for use as the sensitizing antigen for generation of antibodies is not limited by the animal species from which the antibodies are obtained, it is preferably derived from mammals such as humans, mice, or rats with the human-derived protein being most preferred. Human-derived protein can be obtained using the gene sequence or the amino acid sequence disclosed herein.

Proteins that are used as the sensitizing antigen herein may be complete proteins or partial peptides thereof. As the partial peptides of the proteins, for example, N-terminal fragments (N) or C-terminal fragments (C) of the proteins may be mentioned. The term "antibody" as used herein means antibody that reacts to the full-length protein or fragments thereof.

A gene encoding the protein of the present invention or a fragment thereof may be inserted into a known expression system, and said vector is used to transform the host cell described herein to obtain the protein of interest or a fragment thereof from the inside or outside of said host cell by a known method, which may be used as the sensitizing antigen. Alternatively, the cell that expresses the protein or lysates thereof or the chemically synthesized protein of the present invention may be used as sensitizing antigen.

Mammals to be immunized with the sensitizing antigen are not specifically limited, and they are preferably selected in consideration of their compatibility with the parent cell for use in cell fusion. They generally include animals of the order Rodentia, the order Lagomorpha, and the order Primates.

Animals of order.Rodentia include, for example, mice, rats, hamsters, and the like. Animals of order Lagomorpha include, for example, rabbits. Animals of order Primates include, for example, monkeys. As monkeys, catarrhines (Old-World monkeys) such as cynomolgi (crab-eating macaque), rhesus monkeys, sacred baboons, chimpanzees etc. are used.

Immunization of animals with a sensitizing antigen is carried out using a known method. A general method, for example, involves the intraperitoneal or subcutaneous injection of a sensitizing antigen to the mammal. Specifically, a sensitizing antigen which has been diluted and suspended in an appropriate amount of phosphate buffered saline (PBS) or physiological saline is mixed, as desired, with an appropriate amount of a common adjuvant, for example Freund's complete adjuvant. After being emulsified, it is administered to the mammal. Then the sensitizing antigen dissolved at a suitable amount is Freund's incomplete adjuvant is administered for several times every 4 to 21 days. Alternatively a suitable carrier may be used at the time of immunization of the sensitizing antigen. After such immunization, the increase in the desired antibody levels in the serum is confirmed by a conventional method.

In order to obtain polyclonal antibodies, the blood of the mammal that was sensitized with the antigen is removed after the increase in the desired antibody levels in the serum has been confirmed. Serum is separated from the blood by a known method. As polyclonal antibodies, serum containing the polyclonal antibodies may be used, or, as desired, the fraction containing the polyclonal antibodies may be isolated from the serum and used. For example, using an affinity column to which the protein of the present invention has been coupled, a fraction that recognizes the protein of the present invention only is obtained, and this fragment is purified using a Protein A or a Protein G column, to prepare an immunoglobulin G or M.

In order to obtain monoclonal antibodies, immune cells of the mammal that was sensitized with the above antigen are removed and are subjected to cell fusion after the increase in the desired antibody levels in the serum has been confirmed. At this time preferred immune cells that are subjected to cell fusion include, in particular, the spleen cells. The mammalian myeloma cells as the other parent cells which are subjected to cell fusion with the above-mentioned immune cells preferably include myeloma cells of a mammal, more preferably myeloma cells that have acquired a characteristic feature for the selection of fusion cells by a drug.

Cell fusion between the above immune cells and the myeloma cells may be carried out according to the conventional method, for example, the method of Milstein (Galfre, G. and Milstein. C, Methods Enzymol. (1981) 73, 3–46) and the like.

The hybridoma obtained by cell fusion may be selected by culturing in a HAT culture medium (a culture liquid containing hypoxanthine, aminopterin, and thymidine). Culturing in said HAT culture medium is continued generally for a period of time sufficient to effect killing of the cells other than the desired hybridoma (non-fusion cells), generally for several days to several weeks. Then, the conventional limiting dilution method is conducted in which the hybridomas that produce the desired antibody are screened and cloned.

In addition to obtaining the above hybridoma by immunizing an animal other than the human with an antigen, it is also possible to sensitize human lymphocytes, for example lymphocytes infected with EB virus, with a protein, cells expressing them or their lysates in vitro, and to allow the resulting sensitized lymphocytes to be fused with a human-derived myeloma cell having a permanent division potential, for example U266, and thereby to obtain a hybridoma that produces the desired human antibody having the activity of binding the protein (see Japanese Unexamined Patent Publication (Kokai) No. 63-17688).

Then, the hybridoma obtained is transplanted into the abdominal cavity of a mouse, ascites is recovered from the mouse, and the monoclonal antibody obtained is purified and prepared by subjecting it to ammonium sulfate precipitation, Protein A or Protein G column, DEAE ion exchange chromatography, affinity column to which the protein of the present invention has been coupled, and the like. The antibody of the present invention can be used for the purification and detection of the protein of the present invention and, besides, becomes a candidate for the agonist and the antagonist of the protein of the present invention. The antibody may be used for antibody therapy of diseases with which the protein of the present invention is associated. When the antibody obtained is used for the purpose (antibody therapy) of administering to a human body, it is preferably human antibody or humanized antibody in order to reduce immunogenicity.

Furthermore, a transgenic animal having a repertoire of human antibody genes is immunized with the antigen protein, cells expressing them or lysates thereof to obtain the antibody-producing cells, which are used to obtain human antibody against the protein for use in the present invention using hybridomas fused to myeloma cells (see International Patent Application WO 92-03918, WO 93-2227, WO 94-02602, WO 94-25585, WO 96-33735 and WO 96-34096).

In addition to using a hybridoma to produce antibody, antibody-producing immune cells such as sensitized lymphocytes that have been immortalized with an oncogene may be used to obtain antibody.

A monoclonal antibody thus produced can also be obtained as a recombinant antibody by recombinant gene technology (see, for example, Borrebaeck, C. A. K., and Larrick, J. W., THERAPEUTIC MONOCLONAL ANTIBODIES, published in the United Kingdom by MACMILLAN PUBLISHERS LTD., 1990). Recombinant antibody may be produced by cloning DNA encoding it from the hybridoma or an immune cell such as sensitized lymphocytes that produce antibodies, and integrating it into a suitable vector, which is then introduced into a host to produce said antibody. The present invention also encompasses such recombinant antibodies.

Antibodies of the present invention may be antibody fragments or modified versions thereof as long as they bind the protein of the present invention. For example, as fragments of antibody, there may be mentioned Fab, F(ab')2, Fv or single-chain Fv (scFv) in which Fv or Fv's of the H chain and the L chain were ligated via a suitable linker (Huston, J. S. et al., Proc. Natl. Acad. Sci. USA (1988) 85, 5879–5883). Specifically, antibodies are treated with an enzyme such as papain or pepsin, to produce antibody fragments, or genes encoding these antibody fragments are constructed and then introduced into an expression vector, which is then expressed in a suitable host cell (see, for example, Co, M. S. et al., J. Immunol. (1994) 152, 2968–2976; Better, M. and Horwitz, A. H., Methods in Enzymology (1989) 178, 476–496; Pluckthun, A. and Skerra, A., Methods in Enzymol. (1989) 178, 497–515; Lamoyi, E., Methods in Enzymol. (1986) 121, 652–663; Rousseaux, J. et al., Methods in Enzymol. (1986) 121, 663–669; Bird, R. E. and Walker, B. W., Trends Biotechnol. (1991) 9, 132–137).

As modified antibodies, antibodies bound to various molecules such as polyethylene glycol (PEG) can also be used. The term "antibody" as used herein encompasses these modified antibodies. In order to obtain these modified antibodies, the antibody obtained may be chemically modified. These methods are established in the field of the art.

Furthermore, the antibody of the present invention may be obtained as a chimeric antibody comprising a variable region derived from a non-human antibody and a constant region derived from a human antibody, or as a humanized antibody comprising a complementarity determining region (CDR) derived from a non-human antibody and a framework region (FR) and a constant region derived from a human antibody.

Antibodies obtained as described above can be purified to homogeneity. Separation and purification of the antibody for use in the present invention may be accomplished by the separation and the purification methods conventionally used for protein. For example, antibody can be separated and purified by selecting and combining, but not limited to, chromatography columns such as affinity chromatography, filtration, ultrafiltration, salting-out, dialysis, SDS polyacrylamide gel electrophoresis, and isoelectric focusing as appropriate (Antibodies: A Laboratory Manual, Ed Harlow and David Lane, Cold Spring Harbor Laboratory, 1988). The measurement of concentration of the antibody obtained as above can be determined by the measurement of absorbance, enzyme-linked immunosorbent assay (ELISA), and the like.

As columns for use in affinity chromatography, there can be mentioned a Protein A column and a Protein G column. Examples of the columns used in the Protein A column are Hyper D, POROS, Sepharose F. F. (Pharmacia) and the like.

As chromatography other than the above-mentioned affinity chromatography, there can be mentioned, for example, ion exchange chromatography, hydrophobic chromatography, gel-filtration, reverse phase chromatography, adsorption chromatography, and the like (Strategies for Protein Purification and Characterization: A Laboratory Course Manual, Ed Daniel R. Marshak et al., Cold Spring Harbor Laboratory Press, 1996). These chromatographies can be carried out using a liquid chromatography such as HPLC and FPLC.

As the method of determining antibody binding activity of the antibody of the present invention obtained as above, there can be used enzyme-linked immunosorbent assay (ELISA), enzymeimmunoassay (EIA), radioimmunoassay (RIA), or fluorescent antibody assay. When ELISA is used, the protein of the present invention is added to a plate immobilized with the antibody of the present invention, and then a sample containing the antibody of interest, for example a culture supernatant of the antibody-producing cells or purified antibody is added.

The antigen binding activity can be evaluated by adding a second antibody that recognizes the antibody labeled with an enzyme such as alkaline phosphatase, incubating and then washing the plate, and subsequently, after adding the enzyme substrate such as p-nitrophenyl phosphate thereto, determining absorbance. As the protein, a fragment of the protein, a fragment comprising the C-terminal thereof, or a fragment comprising the N-terminal thereof may be used. For the evaluation of activity of the antibody of the present invention, BIAcore (Pharmacia) can be used.

By using these techniques, the method of detecting or determining the protein of the present invention can be performed, said method comprising bringing the antibody of the present invention into contact with a sample expected to contain the protein of the present invention, and detecting or determining an immune complex of said antibody and said protein or immunostaining the cells that express said protein using said antibody.

The method of detecting or determining the protein of the present invention can specifically detect or determine the protein and, therefore, is useful in various experiments using the protein.

The present invention also relates to DNA that specifically hybridizes to DNA (SEQ ID NO: 1) encoding the human WT1 interacting protein or DNA complementary to said DNA, and that has a chain length of at least 15 bases. The term "specifically hybridize" means that there occurs no significant cross-hybridization with DNA encoding other proteins under a standard hybridization conditions, preferably under a stringent hybridization condition. Such DNA includes a probe, a primer, a nucleotide or a nucleotide derivative (for example, antisense oligonucleotide or ribozyme) that can specifically hybridizes to DNA encoding the protein of the present invention or DNA complementary to said DNA. Furthermore, such DNA can be used for the preparation of DNA chips.

The present invention includes, for example, an antisense oligonucleotide that hybridizes to any site in the base sequence of SEQ ID NO: 1. The antisense oligonucleotide is preferably an antisense oligonucleotide against at least 15 or more contiguous nucleotides in the base sequence as set forth in SEQ ID NO: 1. More preferably, it is the above antisense oligonucleotide in which the above contiguous at least 15 or more nucleotides contain a translation initiation codon.

As the antisense oligonucleotide, their derivatives or modified versions may be used. As such modified versions, there can be mentioned, for example, lower alkylphosphonate modified versions such as methyl phosphonate or ethyl phosphonate type, phosphorothioate modified versions, or phosphoramidate modified versions.

As used herein "antisense oligonucleotide" may contain one or a plurality of nucleotide mismatches as long as nucleotides corresponding to nucleotides constituting a given region of DNA or mRNA are all complementary, and DNA or mRNA and the oligonucleotide can specifically hybridize to the base sequence as set forth in SEQ ID NO: 1.

Such DNA is a region of at least 15 contiguous nucleotide sequence and has a homology of at least 70%, at least 80%, and at least 90%, and more preferably 95% or more on the base sequence. The algorithm used for determining homology may be one described herein. Such DNA is useful as a probe for detecting or isolating DNA encoding the protein of the present invention and as a primer for amplifying it as described below.

The antisense oligonucleotide derivative of the present invention binds to DNA or mRNA encoding said protein by acting on the cells that produce the protein of the present invention, thereby inhibit its transcription or translation, or promote the decomposition of mRNA, resulting in the suppression of expression of the protein of the present invention. Eventually it exhibits an effect of suppressing the actions of the protein of the present invention.

The antisense oligonucleotide derivative of the present invention can be mixed with an appropriate base that is inert thereto to formulate an external preparation such as a liniment, a cataplasm and the like.

It can also be mixed, as desired, with an excipient, an isotonic agent, a solubilizer, a stabilizer, an antiseptic, a soothing agent or the like to formulate a tablet, powders, granules, a capsule, a liposome capsule, an injection, a solution, a nasal drop, and the like as well as a lyophilized preparation. They can be prepared according to conventional methods.

The antisense oligonucleotide derivative of the present invention may be applied to the patient by either directly administering to the affected area of the patient or administering into the blood vessel thereby allowing the substance to be delivered to the affected area. Furthermore, an antisense encapsulating material that enhances prolonged action and membrane permeability may be used. There may be mentioned, for example, liposome, poly-L-lysine, lipid, cholesterol, lipofectin or derivatives thereof.

Preferably the dosage of the antisense oligonucleotide derivative of the present invention can be adjusted and a preferred amount can be employed as appropriate depending on the condition of the patient. For example, a preferred dosage is in the range of 0.1 to 100 mg/kg, preferably 0.1 to 50 mg/kg.

The antisense oligonucleotide of the present invention is useful in inhibiting the expression of the protein of the present invention, and thereby in suppressing the biological activity of the protein of the present invention. An inhibitor of expression containing the antisense oligonucleotide of the present invention can suppress the biological activity of the protein of the present invention, and therefore, is useful.

The protein of the present invention is useful for screening compounds that bind thereto. Thus, it is used in a method of screening a compound that binds to the protein of the present invention, said method comprising bringing the protein of the present invention into contact with a test sample expected to contain a compound that binds to said protein, and selecting a compound having an activity of binding to the protein of the present invention.

The protein of the present invention for use in the screening may be a recombinant protein or a naturally occurring protein. Alternatively it may be a partial peptide. Test samples include, but are not limited to, cell extracts, cell culture supernatants, microbial fermentation products, marine organism extracts, plant extracts, purified or roughly purified proteins, peptides, non-peptide compounds, synthetic compounds, and naturally occurring compounds. The protein of the present invention to be contacted with the test sample can be contacted with the test sample as a purified protein, as a form bound to a carrier, and as a fusion protein with another protein.

As a method of screening a protein (ligand etc.) that binds to the present invention using the protein of the present invention, various methods known to a person skilled in the art can be used. Such screening can be performed by, for example, immunoprecipitation. Specifically, it can be carried out as follows. A gene encoding the protein of the present invention is inserted into a vector for expressing foreign genes such as pSV2neo, pcDNA I and pCD8 so as to permit the expression of said gene in an animal cell.

As the promoter used in expression, any commonly used promoters may be used such as SV40 early promoter (Rigby In Williamson (ed.), Genetic Engineering, Vol. 3. Academic Press, London, pp. 83–141 (1982), EF-1 α promoter (Kim et al., Gene 91, 217–223, 1990), CAG promoter (Niwa et al., Gene 108, 193–200, 1991), RSV LTR promoter (Cullen Methods in Enzymology 152, 684–704, 1987), SR α promoter (Takebe et al., Mol. Cell. Biol. 8, 466, 1988), CMV immediate early promoter (Seed and Aruffo, Proc. Natl. Acad. Sci. USA 84, 3365–3369, 1987), SV40 late promoter (Gheysen and Fiers, J. Mol. Appl. Genet. 1, 385–394, 1982), Adenovirus late promoter (Kaufman et al., Mol. Cell. Biol. 9, 946, 1989), and HSV TK promoter.

In order to express a foreign gene by introducing the gene into an animal cell, there are the electroporation method (Chu, G. et al., Nucleic Acids Res. 15, 1311–1326, 1987), the calcium phosphate method (Chen, C and Okayama, H., Mol. Cell. Biol. 7, 2745–2752, 1987), the DEAE dextran method (Lopata, M. A. et al., Nucleic Acids Res. 112, 5707–5717, 1984; Sussman, D. J. and Milman, G., Mol. Cell. Biol. 4, 1642–1643, 1985), the lipofectin method (Derijard, B., Cell 7, 1025–1037, 1994; Lamb, B. T. et al., Nature Genetics 5, 22–30, 1993; Rabindran, S. K. et al., Science 259, 230–234, 1993), and the like, and any of them may be used.

By introducing a recognition site (epitope) of a monoclonal antibody, of which the specificity is known, into the N-terminal or C-terminal of the protein of the present invention, the protein of the present invention can be expressed as a fusion protein having the recognition site of the monoclonal antibody. As the epitope-antibody system, commercially available ones may be used (Jikken Igaku (Experimental Medicine), 13, 85–90, 1995). Vectors are commercially available that permit the expression of fusion proteins with β-galactosidase, maltose-binding protein, glutathione S-transferase, green fuorescence protein (GFP), and the like, via multiple cloning sites.

A method of preparing a fusion protein has also been reported in which a small epitope portion alone comprising a few to about a dozen amino acids is introduced so that the effect of the resulting fusion protein on changes in the property of the protein of the present invention is minimal. For example, an epitope such as poly-histidine (His-tag), influenza hemagglutinin (HA), human c-myc, FLAG, vesicular stomatitis virus glycoprotein (VSV-GP), T7 gene10 protein (T7-tag), herpes simplex virus glycoprotein (HSV-tag), E-tag (epitope on the monoclonal phage) and the like and the monoclonal antibody that recognizes it can be used as the epitope-antibody system for screening proteins that bind to the protein of the present invention (Jikken Igaku (Experimental Medicine) 13, 85–90, 1995).

In immunoprecipitation, an immune complex is formed by adding these antibodies to a cell lysate prepared by using a suitable surfactant. The immune complex comprises the protein of the present invention, a protein capable of binding thereto, and an antibody. In addition to using an antibody to the above epitope, an antibody to the protein of the present invention can also be used to perform immunoprecipitation. The antibody to the protein of the present invention can also be prepared by introducing a gene encoding the protein of the present invention into a suitable E. coli expression vector to express said protein in E. coli, purifying the expressed protein, and then using this to immunize a rabbit, a mouse, a rat, a goat, a chicken, and the like. It can also be prepared by immunizing the above animal with a partial peptide of the protein of the present invention that was synthesized.

An immune complex can be precipitated by using, for example, Protein A Sepharose or Protein G Sepharose when the antibody is a mouse IgG antibody. When the protein of the present invention was prepared as a fusion protein with an epitope such as GST, an immune complex can be formed, as when the antibody of the protein of the present invention was used, by using a substance that specifically binds to these epitopes such as glutathione-Sepharose 4B.

For a general method of immunoprecipitation, it is carried out according to, or persuant to, the method described in an article (Harlow, E. and Lane, D.: Antibodies, pp. 511–552, Cold Spring Harbor Laboratory publications, New York, 1988).

For the analysis of immunoprecipitated protein, SDS-PAGE is generally used, in which the bound protein can be analyzed based on the molecular weight of the protein by using a suitable concentration of gel. At this time, generally the protein bound to the protein of the present invention cannot be detected by a standard staining method for protein such as Coomassie staining or silver staining, and therefore the cells are cultured in a culture liquid containing $^{35}$S-methionine or $^{35}$S-cycteine to label the protein in the cell, which is then detected in order to enhance the sensitivity of detection. If the molecular weight of the protein is known, the protein of interest can be directly purified from the SDS-polyacrylamide gel electrophoresis, and the sequence can be determined.

As a method of isolating a protein bound to said protein using the protein of the present invention, the west western blot (Skolnik, E. Y. et al., Cell (1991) 65, 83–90), for example, can be used. Thus, a cDNA library is constructed using a phage vector (λgt11, ZAP etc.) from a cell, a tissue, and an organ (for example, tissues, cells, and cultured cells such as the heart, the placenta, the testis, the thymus, and peripheral leukocytes) in which the binding protein that binds to the protein of the present invention is expected to be expressed, and to the library is expressed on the LB-agarose to immobilize the expressed protein on a filter. Then the purified and labelled protein of the present invention and the above filter are reacted, and a plaque that expresses the protein bound to the protein of the present invention is detected based on the label.

As methods of labelling the protein of the present invention, there can be mentioned a method of utilizing the binding property of biotin and avidin, a method of utilizing an antibody that specifically binds to the protein of the present invention or a peptide or a polypeptide (for example, GST) fused to the protein of the present invention, a method of utilizing radioisotope, a method of utilizing fluorescence, and the like.

As another aspect of the screening method of the present invention, there can be mentioned a method of conducting a 2-hybrid system (Fields, S. and Sternglanz, R., Trends. Genet. (1994) 10, 286–292) that uses cells. The protein of the present invention is fused to the SRF DNA binding region or the. GAL4 DNA binding region, and then is expressed in yeast cells. From the cells expected to express the protein that binds to the protein of the present invention, a cDNA library is constructed that expresses, in a form fused with the VP16 or the GAL4 transcription activation region, which is introduced into the above yeast cells. From the positive clones detected, library-derived cDNA is isolated and introduced into E. coli for expression (when the protein that binds to the protein of the present invention is expressed in the yeast cells, the binding of the two results in the activation of the reporter gene, and thereby positive clones can be confirmed.).

It is also possible to prepare a protein that binds to the protein of the present invention or the gene thereof using the "two-hybrid system" (MATCHMARKER Two-Hybrid System", "Mammalian MATCHMARKER Two-Hybrid Assay Kit", "MATCHMARKER One-Hybrid System" (all manufactured by Clontech), "HybriZAP Two-Hybrid Vector System" (manufactured by Stratagene), and an article "Dalton S. and Treisman R. (1992) Characterization of SAP-1, a protein recruited by serum response factor to the c-fos serum response element. Cell 68, 597–612"). As the reporter gene, the Ade2 gene, the LacZ gene, the CAT gene, the luciferase gene, the PAI-1 (plasminogen activator inhibitor type 1) gene, and the like can be used in addition to the HIS3 gene.

The screening of a compound that binds to the protein of the present invention can also be effected using affinity chromatography. For example, the protein of the present invention is immobilized onto an affinity column, to which a test sample expected to be expressing a protein that binds to the protein of the present invention is applied. As the test sample in this case, for example, cell extracts, cell lysates and the like may be mentioned. After applying the test sample, the column is washed, and the protein that is bound to the protein of the present invention can be prepared.

The protein obtained is analyzed for its amino acid sequence and, based on the sequence, an oligo DNA is synthesized. Using said DNA as the probe, a DNA library can be screened so that DNA encoding said protein can be obtained.

In accordance with the present invention, as a means to detect or determine the compound that is bound, a biosensor that utilizes the surface plasmon phenomenon can be used. The biosensor that utilizes the surface plasmon phenomenon permits realtime observation, as a surface plasmon resonance signal, of the interaction between the protein of the present invention and the test compound using a trace amount of protein without labeling it (for example, BIAcore, manufactured by Pharmacia). Thus, by using a biosensor such as BIAcore, the binding of the protein of the present invention and the test compound can be evaluated.

As methods of isolating compounds that bind to the protein (including an agonist and an antagonist) of the present invention, in addition to protein, a method in which a synthetic compound, a natural product bank, or a random phage peptide display library is acted onto the immobilized protein of the present invention, and molecules that bind to the protein of the present invention are screened, and a screening method using a high throughput using the combinatorial chemistry technology (Wrighton N C; Farrell F X; Chang R; Kashyap A K; Barbone F P; Mulcahy L S; Johnson D L; Barret R W; Jolliffe L K; Dower W J., Small peptides as potent mimetics of the protein hormone erythropoietin, Science (United States) Jul. 26, 1996, 273 pp. 458–64, Verdine G L., The combinatorial chemistry of nature, Nature (England) Nov. 7, 1996, 384 pp. 11–13, Hogan J C Jr., Directed combinatorial chemistry, Nature (England) Nov. 7, 1996, 384 pp. 17–9) are known to a person skilled in the art.

Furthermore, the present invention relates to a method of screening a compound that promotes or inhibits the activity of protein of the present invention. As the WT1 interacting protein of the present invention has an activity of binding to the WT1 protein and thereby regulating the function of the WT1 protein, this activity can be used as an index to screen a compound that promotes or inhibits the activity of the WT1 interacting protein of the present invention.

The screening method comprises the steps of (a) culturing the cells that express the WT1 interacting protein in the presence of a sample to be tested, (b) detecting the growth of said cells, and (c) selecting a compound that promotes or inhibits said growth as compared to when detected in the absence of a sample to be tested.

The protein used in screening is not specifically limited as long as it has an activity of regulating the function of the WT1 protein. For example, the human WT1 interacting protein can be mentioned, and a protein that is functionally equivalent to this protein can also so be used. Also, the WT1 interacting protein may be intracellularly or extracellularly expressed by the cell.

Test samples are not specifically limited, and there may be mentioned cell extracts, cell culture supernatants, microbial fermentation products, marine organism extracts, plant extracts, purified or roughly purified proteins, peptides, non-peptide compounds, synthetic compounds, and naturally occurring compounds. It is also possible to use the compound obtained in the screening of compounds that bind to the protein of the present invention, as the test compound.

The compound isolated in this screening can be an agonist or an antagonist candidate for the protein of the present invention. The term "agonist" as used herein means a molecule that activates the function of the protein of the present invention by binding thereto. Also the term "antagonist" as used herein means a molecule that suppresses the function of the protein of the present invention by specifically binding thereto. Furthermore, it can be a candidate compound that inhibits the interaction of the molecule (including DNA and protein) that interacts with the protein of the present invention.

The detection of cell growth can be effected by, for example, detecting the measurement of colony forming rate and the determination of the growth rate of the cell, the measurement of cell cycle, and the like.

The compounds isolated from these screenings can become candidate drugs for promoting or inhibiting the activity of the protein of the present invention, and its application into the treatment of diseases (for example cancer) with which the protein of the present invention is associated, is conceivable.

Substances, obtained using the screening method of the present invention, in which part of the structure of compounds that promote or inhibit the activity of the WT1 interacting protein has been modified by addition, deletion and/or substitution is also included in the compounds obtained by the screening method of the present invention.

The present invention also relates to a method of screening a compound that promotes or inhibits the binding of a WT1 interacting protein of the present invention with the WT1 protein. The method comprises the steps of: (a) allowing the WT1 interacting protein to react with the WT1 protein in the presence of a sample to be tested, (b) determining the binding activity of both proteins, and (c) selecting a compound that promotes or inhibits said binding as compared to when detected in the absence of the sample to be tested.

As a method of assaying whether a compound contained in the test sample promotes or inhibits the binding of the present protein and the WT1 protein, there may be mentioned the west western blotting method or a method of quantitating the conjugate of the both proteins in a solution (in vitro) or in the cell (in vivo).

When the compound obtained by the screening method of the present invention is used as a drug for humans and mammals such as mice, rats, guinea pigs, rabbits, chickens, cats, dogs, sheep, pigs, cattle, monkeys, baboons, and chimpanzees, the isolated compound can also be formulated according to a known pharmaceutical method for administration, in addition to directly administering the compound itself to patients.

For example, it can be used either orally as sugar-coated tablets, capsules, elixirs or microcapsules, or parenterally in the form of aseptic solutions with water or another pharmaceutically acceptable liquid or injections of a suspension. For example, conceivably, it is combined with a pharmaceutically acceptable carrier or a medium, specifically sterile water or physiological saline, a plant oil, an emulsifying agent, a suspension, a surfactant, a stabilizer, a flavoring agent, an excipient, a vehicle, a preservative, a binder and the like, and mixed in a unit dosage form, required for commonly recognized pharmaceutical practice, to formulate into a drug. The amount of an active ingredient in these formulations is adjusted to provide a suitable amount in the indicated range.

As additives that can be mixed into tablets or capsules, there can be used, for example, a binder such as gelatin, corn starch, gum tragacanth and gum Arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, gaultheria oil or cherry. When the formulation dosage unit is a capsule, the above materials can further contain liquid carriers like oil and fat. Sterile compositions for injection can be formulated according to a normal pharmaceutical practice using a vehicle such as distilled water for injection.

As an aqueous solution for injection, there can be mentioned, for example, physiological saline, an isotonic liquid containing glucose and another adjuvant, for example, D-sorbitol, D-mannose, D-mannitol and sodium chloride, and may be combined with a suitable solubilizing agent such as alcohol, specifically ethanol, polyalcohol such as propylene glycol, polyethylene glycol, non-ionic surfactant such as polysorbate 80 (™TM), and HCO-50.

As an oleaginous solution, there may be mentioned sesame oil and soy bean oil, and as a solubilizing solution, benzyl benzoate or benzyl alcohol may be used in combination. Furthermore, a buffer such as phosphate buffer, sodium acetate buffer, a soothing agent such as procaine chloride, a stabilizer such as benzyl alcohol and phenol, an antioxidant may be blended. The prepared injection is usually filled into a suitable ampoule.

The administration to patients may be performed by intraarterial injection, intravenous injection, subcutaneous injection, and nasally, transbronchially, intramuscularly, or orally by a method known to a person skilled in the art. The dosage may vary depending on the weight and age of patients, method of administration and the like, and a person skilled in the art can select a suitable dosage as appropriate. Gene therapy is also contemplated in which said DNA is integrated into a vector for gene therapy. The dosage method of administration may vary depending on the weight and age of patients, and the like, and a person skilled in the art can select a suitable dosage as appropriate.

For example, the dosage of a compound that binds to the protein of the present invention or a compound that inhibits the activity of the protein of the present invention may vary depending on the disease condition, but in the case of oral administration, dosage for an adult (assuming body weight being 60 kg) is about 0.1 to 100 mg/day, preferably about 1.0 to 50 mg, and more preferably about 1.0 to 20 mg.

In the case of the parenteral administration, the unit dosage may vary depending on the subject to be administered, the subject organ, disease condition, and the method of administration, but in the form of an injection, a convenient dosage for an adult (assuming body weight being 60 kg) is about 0.01 to 30 mg/day, preferably about 0.1 to 20 mg, and more preferably about 0.1 to 10 mg injected intravenously. For other animals, the amount converted from body weight of 60 kg may be administered.

EXAMPLES

Now the present invention will be explained in more detail hereinbelow.

Example 1

Purification of WTIP (1) Construction and Purification of GST Fusion Protein

Using pBluescript II/WT1(+/+) (Kudoh T. et al., Oncogene, Vol. 13, pp. 1431–1439, 1996) as the template, PCR was conducted using the following primers:

```
1) GST-WT2
5'-TTGAATTCAATGGGCTCCGACGTGCGG-3'     (SEQ ID NO: 3)
5'-TTGTCGACCATGGGATCCTCATGCTT-3'      (SEQ ID NO: 4)

2) GST-WT3
5'-TTGAATTCAATGGGCTCCGACGTGCGG-3'     (SEQ ID NO: 5)
5'-TTGTCGACGAAGACACCGTGCGTGTG-3'      (SEQ ID NO: 6)

3) GST-WT4
5'-TTGAATTCAGATCCAATGGGCCAGCAC-3'     (SEQ ID NO: 7)
5'-TTGTCGACGAAGACACCGTGCGTGTG-3'      (SEQ ID NO: 8)
``` in which an EcoRI recognition sequence has been added to the 5'-end and a NotI recognition sequence has been added to the 3'-end to construct insertion fragments. To the regions that are difficult to amplify, restriction enzyme fragments were inserted via a plasmid as appropriate. The base sequence of the amplified fragment is 1–882 for GST-WT3, 1–546 for GST-WT2, and 541–882 for GST-WT4 (B in FIG. 1). The insertion fragment was integrated into pGEX-5X-3 (Amersham Pharmacia Biotech) and then the sequence was confirmed, and transformed into an *E. coli* strain BL21 (DE3). At this time, pT-Trx, a thioredoxin expression vector, was coexpressed in order to enhance the solubility of the fusion protein (Yasukawa T. et al., J. Biol. Chem. Vol. 270, pp. 25328–25331, 1995).

After confirming expression, an overnight culture was diluted 10-fold and incubated at 37° C. for 1.5 hour, to which isopropyl-β-D-thiogalacto-pyranoside (IPTG) was added to a final concentration of 0.1 mM. After further culturing for 5 hours, the cells were collected, to which a cell dissolution buffer (50 mM Tris-HCl, pH 7.5, 50 mM NaCl, 1 mM EDTA, 1 mM Pefabloc SC (Boehringer Mannheim), 10 µg/ml leupeptin, 1 mM DTT) was added, and solubilized by sonication. The fusion protein in the supernatant was bound to the glutathione Sepharose 4B (Amersham Pharmacia Biotech), and eluted with an elution buffer (50 mM Tris-HCl, pH 7.5, 150 mM NaCl, 20 mM reduced glutathione, 1 mM DTT). The protein concentration was determined by the Bradford method (Protein Assay, Bio-Rad) and bovine serum albumin was used as a standard.

(2) Detection of WTIP by West Western Blot

In order to investigate the presence of the WT1 interacting protein that can be detected with the GST fusion protein in the K562 cells, K562 ($5\times10^6$) was dissolved in 500 µl of the sample buffer for SDS-PAGE, and the west western blot was carried out.

After separating the sample protein on SDS-PAGE, it was transferred to a PVDF membrane (Immobilon-P, Millipore) by the semi-dry method, blocked with TBST (0.05% Tween 20) containing 2% skim milk, and was reacted with 10–20 µg/ml TBS for 1 hour to overnight.

After washing the PVDF membrane with TBST, it was reacted for 1 hour with a 1000-fold dilution of anti-GST antibody (Santa Cruz) in TBST, washed again in TBST, and then reacted for 1 hour with a 8000-fold dilution of anti-mouse IgG antibody (alkaline phosphatase (ALP)-conjugated, or horseradish peroxidase (HRP)-conjugated) in TBST. After washing in TBST and TBS, it was subjected to color development with a NBT/BCIP solution for the ALP-conjugated antibody, and was subjected to light emission with ECL for the HRP-conjugated antibody.

FIG. 2 shows the result of the west western blot. A band at about 115 kDa observed in GST-WT2 and GST-WT3 was not recognized in GST, indicating that this is a specific band showing the presence of the WT1 interacting protein. Furthermore, since the same band was not recognized in GST-WT4, it was shown to have a binding site in the 182 amino acid residues at the N-terminal end of WT1. Since there had been no reports on the WT1 interacting protein of this size (p115), its separation and purification were attempted.

(3) Purification of WTIP

Sample Preparation

After washing the K562 cells ($6\times10^8$ cells) (about 140 mg of protein) in PBS, it was dissolved in 27 ml of the cell dissolution buffer (50 mM Tris-HCl, pH 7.5, 50 mM NaCl, 1 mM EDTA, 1 mM Pefabloc, 10 µg/ml), disrupted by sonication at 60 W for 30 minutes, followed by the addition of 3 ml of the cell dissolution buffer containing 10% SB-12 and further sonication twice at 60 w for 30 minutes, and the final concentration was made 150 mM in 5M NaCl. It was centrifuged to separate the supernatant, filtered with a 0.45 µm filter to prepare a sample for FPLC (Amersham Pharmacia Biotech).

Chromatography

Figure 3:
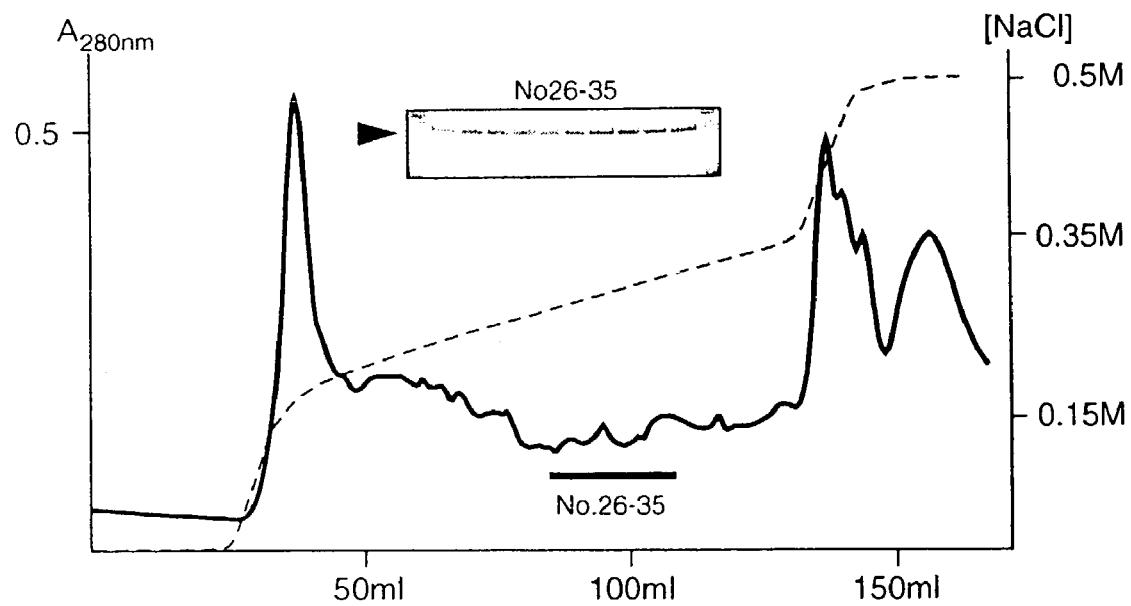
FIG. 3 is a drawing that shows an elution profile wherein the cell-free extracts (the centrifugation supernatant after the sonic disruption of the cells) of the K562 cells were separated by an anion exchange chromatography with HiLoad 16/10 Q Sepharose High Performance. Activity was observed in fraction Nos. 26–35 by the west western blot method.

An anion exchange chromatography was performed using the HiLoad 16/10 Q Sepharose High Performance (Amersham Pharmacia Biotech) and eluted at a flow rate of 2 ml/min with a salt concentration gradient of 0 M to 0.5 M NaCl. The starting buffer was 20 mM Tris-HCl, pH 7.5, 0 M NaCl, 1 mM EDTA, 0.1% CHAPS, and the elution buffer was the starting buffer+0.5 M NaCl. From each of the eluted fractions 20 µl was aliquoted and was subjected to a west western blot using GST-WT3, and the fraction (FIG. 3) for which the WT1 interacting protein was detected was used for the subsequent purification.

Figure 4:
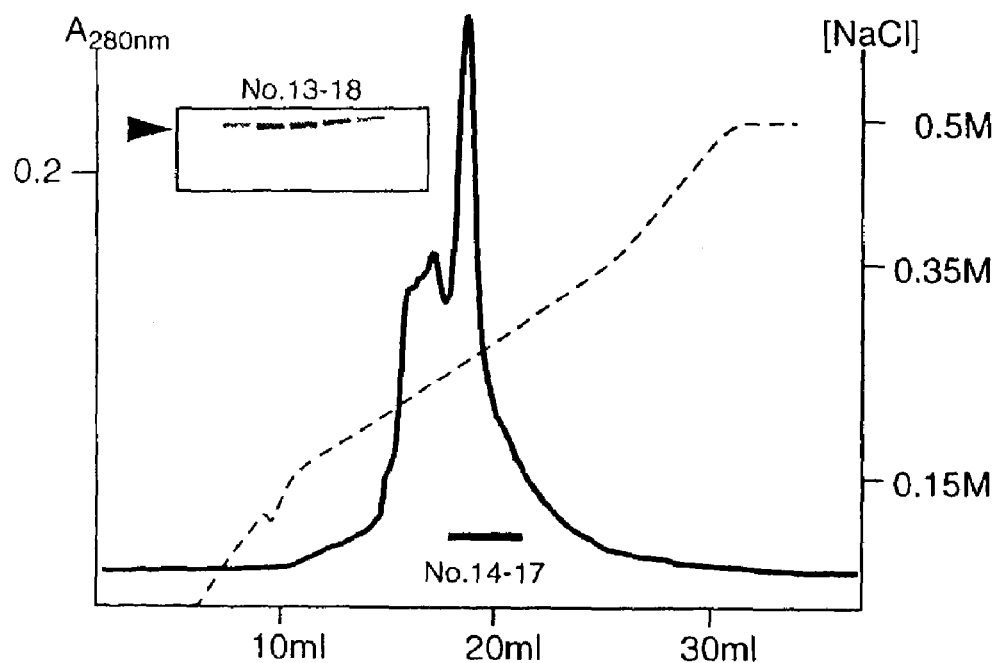
FIG. 4 is a drawing that shows an elution profile wherein the active fractions obtained in FIG. 3 were separated by an anion exchange chromatography with MONO Q HR 5/5. Activity was observed in fraction Nos. 14 to 17 by the west western blot method.
Figure 5:
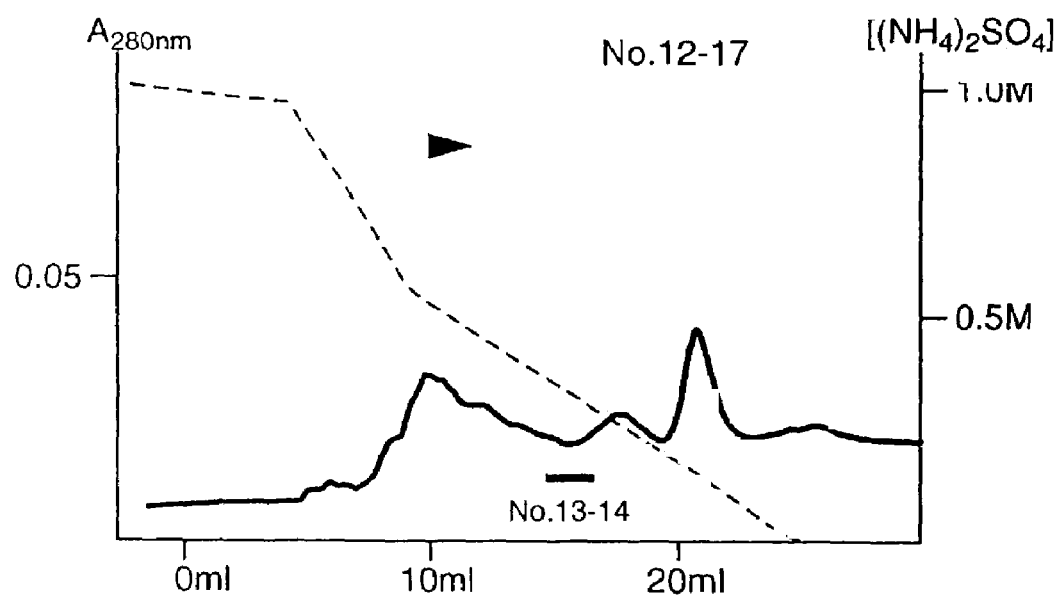
FIG. 5 is a drawing that shows an elution profile wherein the active fractions obtained in FIG. 5 were separated by a hydrophobic chromatography with Phenyl Superrose HR 5/5. Activity was observed in fraction Nos. 13 to 14 by the west western blot method.

Using the same buffer, an anion exchange chromatography was performed using MONO Q HR 5/5 (Amersham Pharmacia Biotech). The flow rate was 1 ml/min. A similar assay was performed for each fraction (FIG. 4). A hydrophobic interaction chromatography was performed using Phenyl Superose HR 5/5 (Amersham Pharmacia Biotech), and then was eluted at a flow rate of 0.5 ml/min and a salt concentration gradient of 1.0 M to 0 M. The starting buffer was 20 mM Tris-HCl, pH 7.5, 1.0 M $(NH_4)2SO_4$, 1 mM EDTA, and the elution buffer was 20 mM Tris-HCl, pH 7.5, 0 M $(NH_4)2SO_4$, 1 mM EDTA. Assay of each fraction was performed by west western blot as in the above, and from the fraction in which the WT1 interacting protein was detected (FIG. 5), protein was recovered with trichloroacetic acid, separated on SDS-PAGE (5.0% gel), transferred to a PVDF membrane (proBlott, Applied Biosystem), and was used for peptide mapping.

Figure 6:
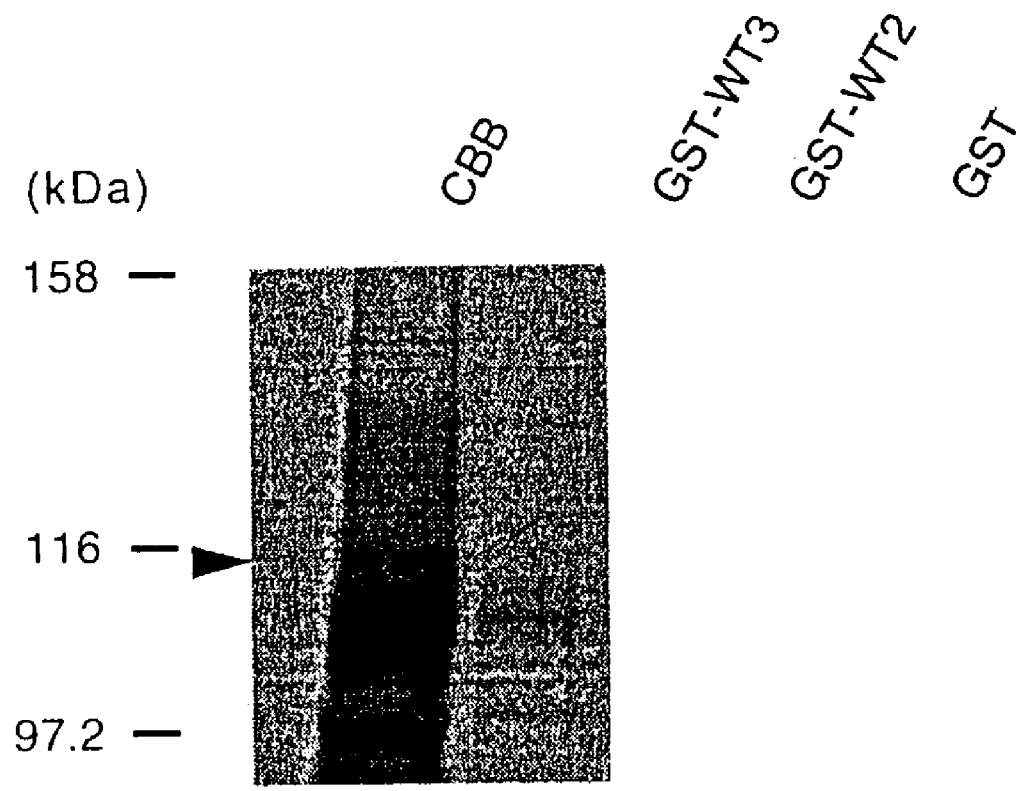
FIG. 6 is an electrophoretogram that shows the result of protein detection with Coomassie brilliant blue (CBB), and the west western blot method detection by the reactivity with GST-WT3, GST-WT2 and GST after the active fractions obtained in FIG. 5 containing 115 kDa protein were transferred to a PVDF membrane. It can be seen that the 115 kDa protein binds to the suppressive domain of WT1.

Thus, as after hydrophobic interaction chromatography, a specific band was separated at around 115 kDa on SDS-PAGE, this was transferred to a PVDF membrane, subjected to CBB staining and west western blot to identify a CBB band (FIG. 6). The bands was excised from the PVDF membrane, and was directly used for peptide mapping.

Peptide Mapping

The protein transferred to the PVDF membrane was decomposed with lysil endopeptidase on the membrane, and after the formed peptide was separated on HPLC, the molecular weight of each peptide was determined by a mass spectrometer (MALDI-TOF MS). The molecular weight pattern of peptides was compared to the amino acid sequence database to predict the original protein.

Identification of WTIP

As a result of peptide mapping, the presence of three different proteins was predicted in the band: HYPA/FGP11 (accession No. AF049528), RNA helicase associated protein (AF083255), and siah binding protein 1 (U51586). The base sequence at the 3'-end has not been determined for HYPA/FBP11, the base sequence at the 5'-end has not been determined for sia binding protein, and the entire sequence of the RNA helicase associated protein has been determined, but the molecular weight was 77.9 kDa which was significantly different from that predicted based on the position of the band. In order to identify the WT1 interacting protein from among them, a his-tagged protein of the known region of each gene was constructed and its binding to GST-WT3 was investigated. As a result, since HYPA/FBP11 bound to GST-WT3, the cloning of the full-length and the identification of the binding site were attempted.

The construction of the above his-tagged protein was performed as follows:

Using cDNA of human leukemia cell line K562 or KG-1 as the template, and the initiation codon of a primer (HYPA/FBP11 (AF049523)) to which a XhoI recognition sequence was added at the 3'-end as 1, PCR was performed for 1–1218 (amino acids 1–406), 1–534 (amino acids 1–178), 1–294 (amino acids 1–98) bases to construct insertion fragments (B in FIG. 7), which were inserted into pET-21b(+) (Novagen) that adds a his tag to the C-terminal. In almost the same manner as for the GST fusion protein, E. coli was cultured, and the cells were recovered. However, pT-Trx was not used. The cells derived from 1 ml of the culture were dissolved in 100 µl of the sample buffer for SDS-PAGE, and were directly used for west western blot and Western blot. The antibody used in Western blot was anti-His tag antibody (c-term, Invitrogen).

Example 2

Cloning of cDNA Encoding WTIP

WTIP has a full length of about 3 kbp, and about 1.3 kbp at the 5'-end is HYPA/FBP11. This contains the WW domain that is known to bind to a proline-rich domain. Since the full-length of a mouse homolog of FBP11 was reported, cDNA derived from K562 and from KG-1 was amplified using the sequence at the 3'-end, and an about 3 kbp fragment was obtained.

Using the cDNA of K562, PCR and RACE (RApid Amplification of cDNA ends) were performed from the known sequences. First, for the 5'-end, 5' RACE was performed using a base sequence 5'-CTTTGCTGGTTG-GCTCTCCTCCTCTTCT-3' (SEQ ID NO: 9) in a known region as the antisense primer to confirm the 5'-end of the known sequence.

For the 3'-end, using a base sequence 5'-TTGATCAT-CATCCAGTTGCTCCAAAAGGG-3' (SEQ ID NO: 10) corresponding to the C-terminal of the mouse FBP11 translation region as the antisense primer and a base sequence 5'-TGGGACAAATGCCTGGAATGATGTCGTC-3' (SEQ ID NO: 11) in HYPA as the sense primer, PCR was performed to determine the base sequence, and it was found that this region contained NY-REN-6.

Furthermore, using a base sequence 5'-CAGCGATCA-GAGTCTCGTTCTGCTTCAG-3' (SEQ ID NO: 12) in the NY-REN-6 region as the sense primer, 3' RACE was performed to determine the base sequence. By combining these fragments, the full-length of WTIP was cloned.

An about 3 kbp DNA fragment obtained as above encodes the full-length of human WTIP, and the base sequence is shown in SEQ ID NO: 1 and the deduced amino acid sequence in SEQ ID NO: 2. The determination of the base sequence was performed by the TA cloning (Invitrogen) of cDNA. For DNA database search, Basic BLAST (BLAST 2.0) on the NCBI server was used. For the analysis of the base sequence, GENETYX-Mac 10.1 (SDC Software Development Institute) was used.

Figure 7:
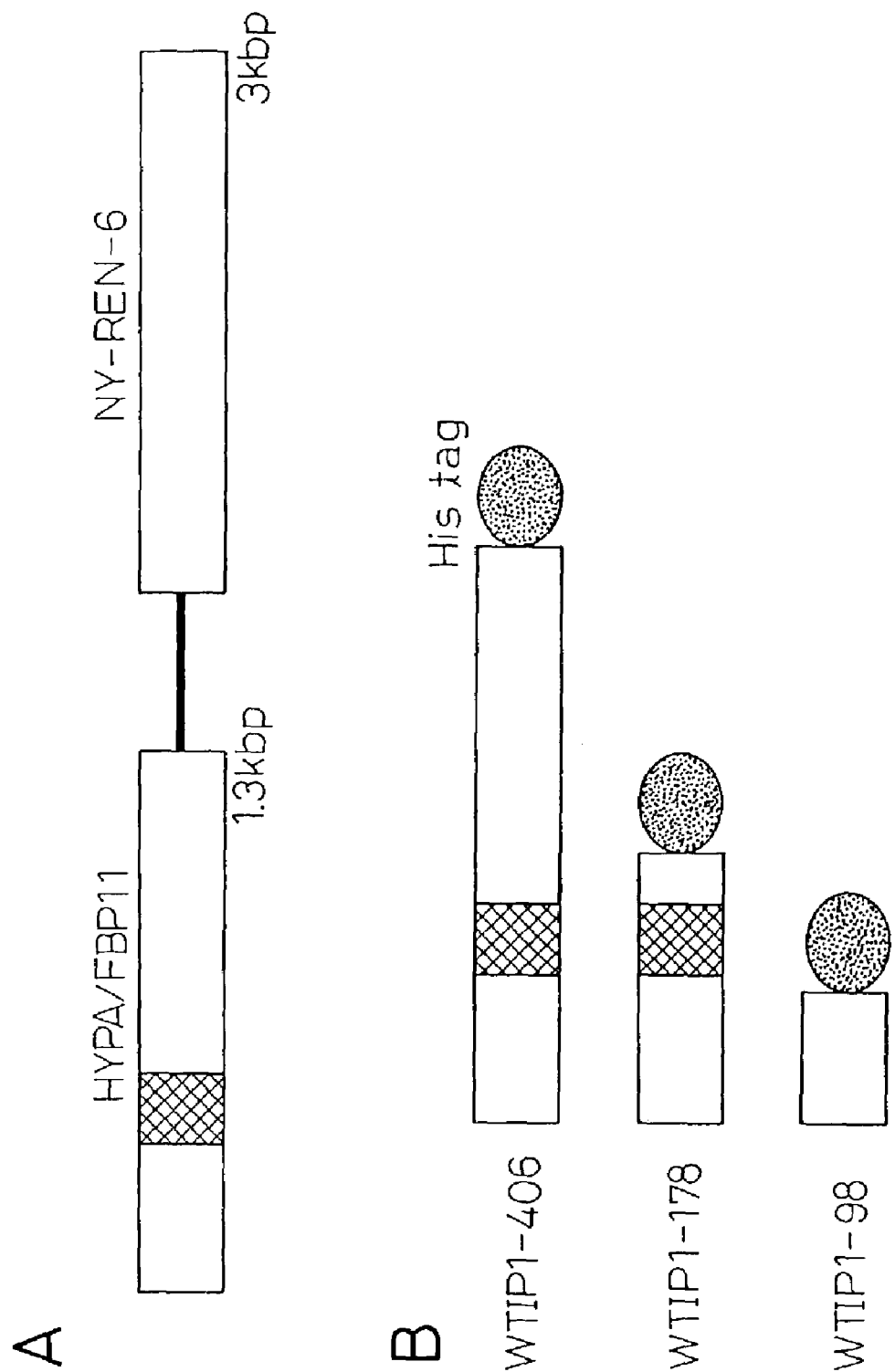
In FIG. 7, A shows the structure of the full-length WTIP, B shows the structure of polypeptides (WTIP 1-406 and WTIP 1-178) containing the WW domain at the N-terminal end of WTIP and a polypeptide (WTIP 1-98) containing no WW domains in which a histidine (His) tag (tag) has been attached to the C-terminal of each polypeptide.

The structure of full-length WITP is shown in FIG. 7.

Example 3

WT1 Interaction Site for WTIP

Figure 8:
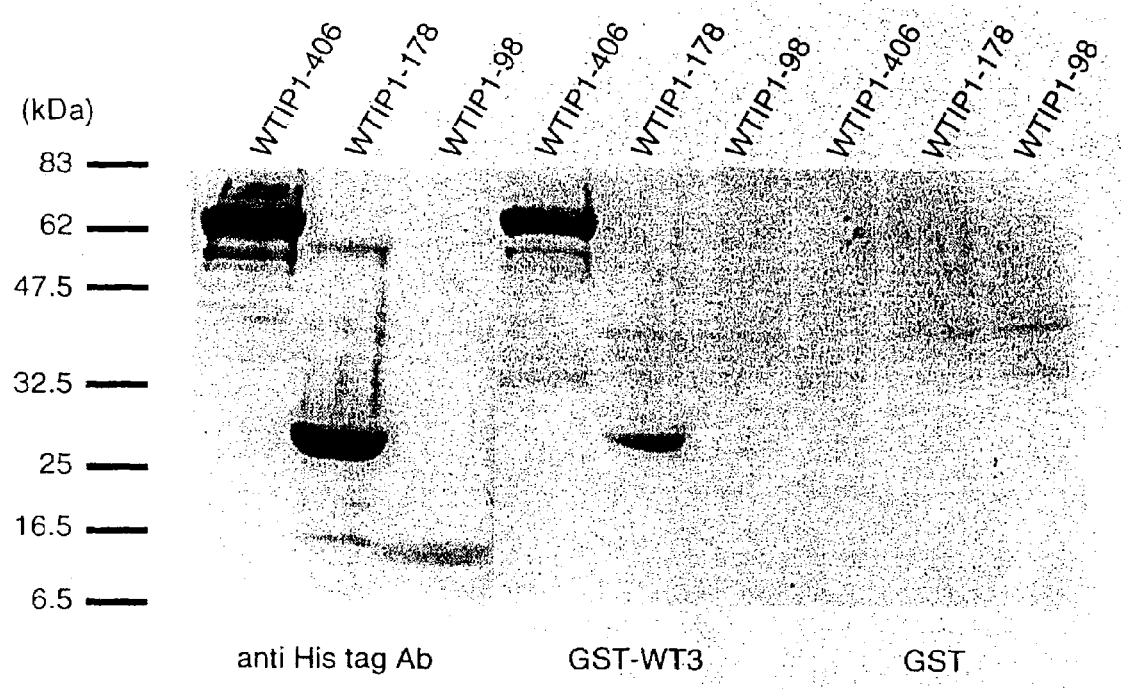
FIG. 8 is an electrophoretogram that shows the result of detection by the reactivity with anti-His tagged polypeptide antibody, GST-WT3, and GST after the polypeptide shown in FIG. 7 was electrophoresed. It can be seen that WTIP 1-406 and WTIP 1-178 containing the WW domain react, but that WTIP 1-98, that does not contain the WW domain, does not react, with GST-WT3 that contains the suppressive domain, and GST that does not contain the suppressive domain does not react with any of the WTIP fragments, indicating that the WW domain in WTIP and a part of the suppressive domain of the WT1 protein react.

The WW domain is known to bind to a prolin-rich domain having the Pro-ProLeu-Pro (PPLP) (SEQ ID NO: 15) motif, but the same motif cannot be found in Huntingtin. Though WT1 also has the proline-rich domain, it is not a PPLP (SEQ ID NO: 15) motif. In order to investigate whether WT1 is bound to WTIP via the WW domain, west western blot was performed using a his-tagged protein of a WTIP mutant. As shown in FIG. 8, a mutant containing no WW domain had lost the ability of binding with GST-WT3, indicating that the WW domain is required for the binding of WTIP and WT1.

Example 4

Reactivity of WT1 and WTIP in the Cell

Using a cell line U937 in which WT1 was forcefully expressed, a co-precipitation experiment by immunoprecipitation was performed to confirm the binding of WT1 and WTIP in the cell.

$1 \times 10^7$ cells were dissolved in 500 µl of the ELB buffer (50 mM HEPES, pH 7.5, 250 mM NaCl, 0.5 mM EDTA, 0.1% NP-40, 1 mM Pefabloc (™TM), Complete (™TM) EDTA free, 1 mM DTT), disrupted by sonication, allowed to stand on ice for 1 hour, and centrifuged at 15000 rpm, 4° C. to recover the supernatant. To the supernatant was added 4 µg of anti-WT1 antibody (C-19, Santa-Cruz), gently stirred at 4° C. for 2 hours, and then 20 µl (bed volume) of Protein A Sepharose (Amersham Pharmacia Biotech) was added, and was further stirred for 2 hours. After washing the Protein A Sepharose 3 times with 1 mL of the ELB buffer, 40 µl of the sample buffer for SDS-PAGE was added. The reaction supernatant was recovered as the flow through, to which the sample buffer was similarly added. The two were heated to 90° C. for 5 minutes, and was subjected to Western blot. After electrophoresis on a 7.5% polyacrylamide gel, it was transferred to Immobilon P (Millipore), and was subjected to color development with NBT/BCIP using anti-WTIP antibody as the primary antibody and anti-rabbit IgG antibody (alkaline phosphatase-conjugated, Promega) as the second antibody.

Figure 9:
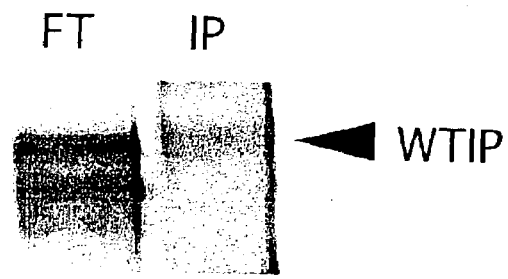
FIG. 9 is an electrophoretogram that shows that WT1 and WTIP bind in the cell.

In FIG. 9, FT represents flow through and IP represents the binding fraction of Protein A Sepharose. At the position of the arrowhead in FIG. 9, a band of WTIP was observed. Thus, it was shown that WT1 and WTIP bind in the cells in which WT1 was forcefully expressed.

The invention claimed is:

1. An isolated WT1 interacting protein comprising the amino acid sequence as set forth in SEQ ID NO: 2.

2. An isolated protein that is encoded by DNA comprising the nucleotide sequence as set forth in SEQ ID NO: 1.

3. An isolated function modulator of the WT1 protein comprising as an active ingredient a polypeptide consisting of the amino acid sequence as set forth in SEQ ID NO: 2.

4. A method of producing a protein comprising culturing an isolated host cell comprising a vector that comprising a sequence encoding the protein according to claim 1.

5. A method of screening a compound that binds to a protein according to claim or a partial peptide thereof 1, said method comprising:
   (a) bringing a sample to be tested into contact with said protein or said partial peptide thereof;
   (b) detecting the binding activity of said sample with said protein of said partial peptide thereof; and
   (c) selecting a compound comprising an activity of binding to said protein or said partial peptide thereof.

* * * * *

SEQUENCE LISTING

```
<160> NUMBER OF SEQ ID NOS: 15

<210> SEQ ID NO 1
<211> LENGTH: 2979
<212> TYPE: DNA
<213> ORGANISM: Homo sapiens
<220> FEATURE:
<223> OTHER INFORMATION: Nucleotide sequence encoding human WTIP
<220> FEATURE:
<221> NAME/KEY: CDS
<222> LOCATION: (14)..(2884)

<400> SEQUENCE: 1
tctgagcccg acg atg agg ccg ggg acg gga gct gag cgt gga ggc ctc          49
            Met Arg Pro Gly Thr Gly Ala Glu Arg Gly Gly Leu
                1               5                  10 atg gtg agt gaa atg gag agc cat cct ccc tcg cag ggt cct ggg gac          97
Met Val Ser Glu Met Glu Ser His Pro Pro Ser Gln Gly Pro Gly Asp
    15                  20                  25
```

-continued

| | |
|---|---|
| ggg gag cgg aga ttg tcc ggc tca agc ctc tgc tcc ggc tct tgg gtc<br>Gly Glu Arg Arg Leu Ser Gly Ser Ser Leu Cys Ser Gly Ser Trp Val<br>30                         35                      40 | 145 |
| tct gct gac ggc ttc ctg agg aga cgg ccc tcg atg ggg cac cct ggc<br>Ser Ala Asp Gly Phe Leu Arg Arg Arg Pro Ser Met Gly His Pro Gly<br>45                         50                      55                      60 | 193 |
| atg cat tat gcc cca atg gga atg cac cct atg ggt cag aga gcg aat<br>Met His Tyr Ala Pro Met Gly Met His Pro Met Gly Gln Arg Ala Asn<br>                    65                      70                         75 | 241 |
| atg cct cct gta cct cat gga atg atg ccg cag atg atg ccc cct atg<br>Met Pro Pro Val Pro His Gly Met Met Pro Gln Met Met Pro Pro Met<br>                    80                         85                         90 | 289 |
| gga ggg cca cca atg gga caa atg cct gga atg atg tcg tca gta atg<br>Gly Gly Pro Pro Met Gly Gln Met Pro Gly Met Met Ser Ser Val Met<br>                95                        100                     105 | 337 |
| cct gga atg atg atg tct cat atg tct cag gct tcc atg cag cct gcc<br>Pro Gly Met Met Met Ser His Met Ser Gln Ala Ser Met Gln Pro Ala<br>      110                     115                     120 | 385 |
| tta ccg cca gga gta aat agt atg gat gta gca gca ggt aca gca tct<br>Leu Pro Pro Gly Val Asn Ser Met Asp Val Ala Ala Gly Thr Ala Ser<br>125                       130                     135                     140 | 433 |
| ggt gca aaa tca atg tgg act gaa cat aaa tca cct gat gga agg act<br>Gly Ala Lys Ser Met Trp Thr Glu His Lys Ser Pro Asp Gly Arg Thr<br>                    145                     150                     155 | 481 |
| tac tac tac aac act gaa acc aaa cag tct acc tgg gag aaa cca gat<br>Tyr Tyr Tyr Asn Thr Glu Thr Lys Gln Ser Thr Trp Glu Lys Pro Asp<br>                    160                     165                     170 | 529 |
| gat ctt aaa aca cct gct gag caa ctc tta tct aaa tgc ccc tgg aag<br>Asp Leu Lys Thr Pro Ala Glu Gln Leu Leu Ser Lys Cys Pro Trp Lys<br>                      175                     180                     185 | 577 |
| gaa tac aaa tca gat tct gga aag cct tac tat tat aat tct caa aca<br>Glu Tyr Lys Ser Asp Ser Gly Lys Pro Tyr Tyr Tyr Asn Ser Gln Thr<br>                    190                     195                     200 | 625 |
| aaa gaa tct cgc tgg gcc aaa cct aaa gaa ctt gag gat ctt gaa gga<br>Lys Glu Ser Arg Trp Ala Lys Pro Lys Glu Leu Glu Asp Leu Glu Gly<br>205                       210                     215                     220 | 673 |
| tac cag aat acc att gtt gct gga agt ctt att aca aaa tca aac ctg<br>Tyr Gln Asn Thr Ile Val Ala Gly Ser Leu Ile Thr Lys Ser Asn Leu<br>                    225                     230                     235 | 721 |
| cat gca atg atc aaa gct gaa gaa agc agt aag caa gaa gag tgc acc<br>His Ala Met Ile Lys Ala Glu Glu Ser Ser Lys Gln Glu Glu Cys Thr<br>                    240                     245                     250 | 769 |
| aca aca tca aca gcc cca gtc cct aca aca gaa att ccg acc aca atg<br>Thr Thr Ser Thr Ala Pro Val Pro Thr Thr Glu Ile Pro Thr Thr Met<br>255                       260                     265 | 817 |
| agc acc atg gct gct gcc gaa gca gca gct gct gtt gtt gca gca gca<br>Ser Thr Met Ala Ala Ala Glu Ala Ala Ala Ala Val Val Ala Ala Ala<br>      270                     275                     280 | 865 |
| gca gcg gca gca gca gca gca gct gca gcc aat gct aat gct tcc act<br>Ala Ala Ala Ala Ala Ala Ala Ala Ala Ala Asn Ala Asn Ala Ser Thr<br>285                       290                     295                     300 | 913 |
| tct gct tct aat act gtc agt gga act gtt cca gtt gtt cct gag cct<br>Ser Ala Ser Asn Thr Val Ser Gly Thr Val Pro Val Val Pro Glu Pro<br>                    305                     310                     315 | 961 |
| gaa gtt act tcc att gtt gct act gtt gta gat aat gag aat aca gta<br>Glu Val Thr Ser Ile Val Ala Thr Val Val Asp Asn Glu Asn Thr Val<br>                    320                     325                     330 | 1009 |
| act att tca act gag gaa caa gca caa ctt act agt acc cct gct att<br>Thr Ile Ser Thr Glu Glu Gln Ala Gln Leu Thr Ser Thr Pro Ala Ile<br>                    335                     340                     345 | 1057 |

-continued

| | | |
|---|---|---|
| cag gat caa agt gtg gaa gta tcc agt aat act gga gaa gaa aca tct<br>Gln Asp Gln Ser Val Glu Val Ser Ser Asn Thr Gly Glu Glu Thr Ser<br>350                                 355                               360 | | 1105 |
| aag caa gaa act gta gct gat ttt act ccc aaa aaa gag gag gag<br>Lys Gln Glu Thr Val Ala Asp Phe Thr Pro Lys Lys Glu Glu Glu<br>365                       370                               375                      380 | | 1153 |
| agc caa cca gca aag aaa aca tac act tgg aat aca aag gaa gag gca<br>Ser Gln Pro Ala Lys Lys Thr Tyr Thr Trp Asn Thr Lys Glu Glu Ala<br>                            385                               390                           395 | | 1201 |
| aag caa gct ttt aaa gaa tta ttg aaa gaa aag cgg gta cca tcg aat<br>Lys Gln Ala Phe Lys Glu Leu Leu Lys Glu Lys Arg Val Pro Ser Asn<br>400                                405                               410 | | 1249 |
| gct tca tgg gag cag gct atg aaa atg att att aat gat cca cga tac<br>Ala Ser Trp Glu Gln Ala Met Lys Met Ile Ile Asn Asp Pro Arg Tyr<br>                415                               420                           425 | | 1297 |
| agt gct ttg gca aag tta agt gaa aaa aag caa gcc ttt aat gcc tat<br>Ser Ala Leu Ala Lys Leu Ser Glu Lys Lys Gln Ala Phe Asn Ala Tyr<br>430                                435                              440 | | 1345 |
| aaa gtc cag aca gaa aaa gaa gaa aaa gaa gaa gca aga tca aag tac<br>Lys Val Gln Thr Glu Lys Glu Glu Lys Glu Glu Ala Arg Ser Lys Tyr<br>445                                450                             455                      460 | | 1393 |
| aaa gag gct aag gaa tcc ttt cag cgt ttt ctt gaa aat cat gag aaa<br>Lys Glu Ala Lys Glu Ser Phe Gln Arg Phe Leu Glu Asn His Glu Lys<br>                            465                               470                           475 | | 1441 |
| atg act tct aca acc aga tac aaa aaa gca gag caa atg ttt gga gag<br>Met Thr Ser Thr Thr Arg Tyr Lys Lys Ala Glu Gln Met Phe Gly Glu<br>480                                485                              490 | | 1489 |
| atg gaa gtt tgg aat gca ata tca gaa cgt gat cgt ctt gaa atc tat<br>Met Glu Val Trp Asn Ala Ile Ser Glu Arg Asp Arg Leu Glu Ile Tyr<br>                495                               500                           505 | | 1537 |
| gaa gat gtt ttg ttc ttt ctt tca aaa aaa gaa aag gaa caa gca aag<br>Glu Asp Val Leu Phe Phe Leu Ser Lys Lys Glu Lys Glu Gln Ala Lys<br>510                                515                              520 | | 1585 |
| cag ttg cga aag aga aat tgg gaa gcc tta aaa aac ata ctt gac aac<br>Gln Leu Arg Lys Arg Asn Trp Glu Ala Leu Lys Asn Ile Leu Asp Asn<br>525                                530                              535                      540 | | 1633 |
| atg gct aat gta aca tac tct acc act tgg tct gaa gcc cag cag tat<br>Met Ala Asn Val Thr Tyr Ser Thr Thr Trp Ser Glu Ala Gln Gln Tyr<br>                            545                               550                           555 | | 1681 |
| ctg atg gat aat cca act ttt gca gaa gat gag gag tta caa aat atg<br>Leu Met Asp Asn Pro Thr Phe Ala Glu Asp Glu Glu Leu Gln Asn Met<br>560                                565                              570 | | 1729 |
| gac aaa gaa gat gca tta att tgc ttt gaa gaa cac att cgg gct tta<br>Asp Lys Glu Asp Ala Leu Ile Cys Phe Glu Glu His Ile Arg Ala Leu<br>                            575                               580                           585 | | 1777 |
| gaa aag gag gaa gaa gaa gaa aaa cag aag agt ttg ctg aga gaa agg<br>Glu Lys Glu Glu Glu Glu Glu Lys Gln Lys Ser Leu Leu Arg Glu Arg<br>590                                595                              600 | | 1825 |
| aga cga cag cga aaa aat agg gaa tct ttc cag ata ttt tta gat gaa<br>Arg Arg Gln Arg Lys Asn Arg Glu Ser Phe Gln Ile Phe Leu Asp Glu<br>605                                610                              615                      620 | | 1873 |
| tta cat gaa cat gga caa ctg cat tct atg tca tct tgg atg gaa ttg<br>Leu His Glu His Gly Gln Leu His Ser Met Ser Ser Trp Met Glu Leu<br>                            625                               630                           635 | | 1921 |
| tat cca act att agt tct gat att aga ttc act aat atg ctt ggt cag<br>Tyr Pro Thr Ile Ser Ser Asp Ile Arg Phe Thr Asn Met Leu Gly Gln<br>640                                645                              650 | | 1969 |
| cct gga tca act gca ctt gat ctt ttc aag ttt tat gtt gag gat ctt<br>Pro Gly Ser Thr Ala Leu Asp Leu Phe Lys Phe Tyr Val Glu Asp Leu<br>                            655                               660                           665 | | 2017 |

```
aaa gca cgt tat cat gac gag aag aag ata ata aaa gac att cta aag    2065
Lys Ala Arg Tyr His Asp Glu Lys Lys Ile Ile Lys Asp Ile Leu Lys
        670                 675                 680 gat aaa gga ttt gta gtt gaa gta aac act act ttt gaa gat ttt gtg    2113
Asp Lys Gly Phe Val Val Glu Val Asn Thr Thr Phe Glu Asp Phe Val
685                 690                 695                 700 gcg ata atc agt tca act aaa aga tca act aca tta gat gct gga aat    2161
Ala Ile Ile Ser Ser Thr Lys Arg Ser Thr Thr Leu Asp Ala Gly Asn
        705                 710                 715 atc aaa ttg gct ttc aat agt tta cta gaa aag gca gaa gcc cgt gaa    2209
Ile Lys Leu Ala Phe Asn Ser Leu Leu Glu Lys Ala Glu Ala Arg Glu
        720                 725                 730 cgt gaa aga gaa aaa gaa gag gct cgg aag atg aaa cga aaa gaa tct    2257
Arg Glu Arg Glu Lys Glu Glu Ala Arg Lys Met Lys Arg Lys Glu Ser
        735                 740                 745 gca ttt aag agt atg tta aaa caa gct gct cct ccg ata gaa ttg gat    2305
Ala Phe Lys Ser Met Leu Lys Gln Ala Ala Pro Pro Ile Glu Leu Asp
        750                 755                 760 gct gtc tgg gaa gat atc cgt gag aga ttt gta aaa gag cca gca ttt    2353
Ala Val Trp Glu Asp Ile Arg Glu Arg Phe Val Lys Glu Pro Ala Phe
765                 770                 775                 780 gag gac ata act cta gaa tct gaa aga aaa cga ata ttt aaa gat ttt    2401
Glu Asp Ile Thr Leu Glu Ser Glu Arg Lys Arg Ile Phe Lys Asp Phe
        785                 790                 795 atg cat gtg ctt gag cat gaa tgt cag cat cat cat tca aag aac aag    2449
Met His Val Leu Glu His Glu Cys Gln His His His Ser Lys Asn Lys
        800                 805                 810 aaa cat tct aag aaa tct aaa aaa cat cat agg aaa cgt tcc cgc tct    2497
Lys His Ser Lys Lys Ser Lys Lys His His Arg Lys Arg Ser Arg Ser
        815                 820                 825 cga tcg ggg tca gat tca gat gat gat gat agc cat tca aag aaa aaa    2545
Arg Ser Gly Ser Asp Ser Asp Asp Asp Asp Ser His Ser Lys Lys Lys
830                 835                 840 aga cag cga tca gag tct cgt tct gct tca gaa cat tct tct agt gca    2593
Arg Gln Arg Ser Glu Ser Arg Ser Ala Ser Glu His Ser Ser Ser Ala
845                 850                 855                 860 gag tct gag aga agt tat aaa aag tca aaa aag cat aag aag aaa agt    2641
Glu Ser Glu Arg Ser Tyr Lys Lys Ser Lys Lys His Lys Lys Lys Ser
        865                 870                 875 aag aag agg aga cat aaa tct gac tct cca gaa tcc gat gct gag cga    2689
Lys Lys Arg Arg His Lys Ser Asp Ser Pro Glu Ser Asp Ala Glu Arg
        880                 885                 890 gag aag gat aaa aaa gaa aaa gat cgg gaa agt gaa aaa gac aga act    2737
Glu Lys Asp Lys Lys Glu Lys Asp Arg Glu Ser Glu Lys Asp Arg Thr
        895                 900                 905 aga caa aga tca gaa tca aaa cac aaa tcg cct aag aaa aag act gga    2785
Arg Gln Arg Ser Glu Ser Lys His Lys Ser Pro Lys Lys Lys Thr Gly
910                 915                 920 aag gat tct ggt aat tgg gat act tct ggc agc gaa ctg agt gaa ggg    2833
Lys Asp Ser Gly Asn Trp Asp Thr Ser Gly Ser Glu Leu Ser Glu Gly
925                 930                 935                 940 gaa ttg gaa aag cgc aga aga acc ctt ttg gag caa ctg gat gat gat    2881
Glu Leu Glu Lys Arg Arg Arg Thr Leu Leu Glu Gln Leu Asp Asp Asp
                945                 950                 955 caa taaattatac caaatatatg tttacagtat gatttaaagt ctgattcaga         2934
Gln ccagggactc tatttttaaag ttcaactgaa ataacactgg gaaaa                 2979
```

<210> SEQ ID NO 2
<211> LENGTH: 957
<212> TYPE: PRT
<213> ORGANISM: Homo sapiens
<220> FEATURE:
<223> OTHER INFORMATION: Amino aicd sequence human WTIP

<400> SEQUENCE: 2

```
Met Arg Pro Gly Thr Gly Ala Glu Arg Gly Gly Leu Met Val Ser Glu
  1               5                  10                  15

Met Glu Ser His Pro Ser Gln Gly Pro Gly Asp Gly Glu Arg Arg
             20                  25                  30

Leu Ser Gly Ser Ser Leu Cys Ser Gly Ser Trp Val Ser Ala Asp Gly
             35                  40                  45

Phe Leu Arg Arg Arg Pro Ser Met Gly His Pro Gly Met His Tyr Ala
 50                  55                  60

Pro Met Gly Met His Pro Met Gly Gln Arg Ala Asn Met Pro Pro Val
 65                  70                  75                  80

Pro His Gly Met Met Pro Gln Met Met Pro Pro Met Gly Gly Pro Pro
                 85                  90                  95

Met Gly Gln Met Pro Gly Met Met Ser Ser Val Met Pro Gly Met Met
                100                 105                 110

Met Ser His Met Ser Gln Ala Ser Met Gln Pro Ala Leu Pro Pro Gly
            115                 120                 125

Val Asn Ser Met Asp Val Ala Ala Gly Thr Ala Ser Gly Ala Lys Ser
130                 135                 140

Met Trp Thr Glu His Lys Ser Pro Asp Gly Arg Thr Tyr Tyr Tyr Asn
145                 150                 155                 160

Thr Glu Thr Lys Gln Ser Thr Trp Glu Lys Pro Asp Asp Leu Lys Thr
                165                 170                 175

Pro Ala Glu Gln Leu Leu Ser Lys Cys Pro Trp Lys Glu Tyr Lys Ser
            180                 185                 190

Asp Ser Gly Lys Pro Tyr Tyr Tyr Asn Ser Gln Thr Lys Glu Ser Arg
        195                 200                 205

Trp Ala Lys Pro Lys Glu Leu Glu Asp Leu Glu Gly Tyr Gln Asn Thr
    210                 215                 220

Ile Val Ala Gly Ser Leu Ile Thr Lys Ser Asn Leu His Ala Met Ile
225                 230                 235                 240

Lys Ala Glu Glu Ser Ser Lys Gln Glu Glu Cys Thr Thr Thr Ser Thr
                245                 250                 255

Ala Pro Val Pro Thr Thr Glu Ile Pro Thr Thr Met Ser Thr Met Ala
            260                 265                 270

Ala Ala Glu Ala Ala Ala Ala Val Ala Ala Ala Ala Ala Ala
        275                 280                 285

Ala Ala Ala Ala Ala Ala Asn Ala Asn Ala Ser Thr Ser Ala Ser Asn
        290                 295                 300

Thr Val Ser Gly Thr Val Pro Val Pro Glu Pro Glu Val Thr Ser
305                 310                 315                 320

Ile Val Ala Thr Val Asp Asn Glu Asn Thr Val Thr Ile Ser Thr
                325                 330                 335

Glu Glu Gln Ala Gln Leu Thr Ser Thr Pro Ala Ile Gln Asp Gln Ser
            340                 345                 350

Val Glu Val Ser Ser Asn Thr Gly Glu Glu Thr Ser Lys Gln Glu Thr
        355                 360                 365
```

```
Val Ala Asp Phe Thr Pro Lys Lys Glu Glu Glu Ser Gln Pro Ala
    370                 375                 380

Lys Lys Thr Tyr Thr Trp Asn Thr Lys Glu Glu Ala Lys Gln Ala Phe
385                     390                 395                 400

Lys Glu Leu Leu Lys Glu Lys Arg Val Pro Ser Asn Ala Ser Trp Glu
                405                 410                 415

Gln Ala Met Lys Met Ile Ile Asn Asp Pro Arg Tyr Ser Ala Leu Ala
            420                 425                 430

Lys Leu Ser Glu Lys Lys Gln Ala Phe Asn Ala Tyr Lys Val Gln Thr
        435                 440                 445

Glu Lys Glu Lys Glu Glu Ala Arg Ser Lys Tyr Lys Glu Ala Lys
    450                 455                 460

Glu Ser Phe Gln Arg Phe Leu Glu Asn His Glu Lys Met Thr Ser Thr
465                 470                 475                 480

Thr Arg Tyr Lys Lys Ala Glu Gln Met Phe Gly Glu Met Glu Val Trp
                485                 490                 495

Asn Ala Ile Ser Glu Arg Asp Arg Leu Glu Ile Tyr Glu Asp Val Leu
            500                 505                 510

Phe Phe Leu Ser Lys Lys Glu Lys Glu Gln Ala Lys Gln Leu Arg Lys
        515                 520                 525

Arg Asn Trp Glu Ala Leu Lys Asn Ile Leu Asp Asn Met Ala Asn Val
530                 535                 540

Thr Tyr Ser Thr Thr Trp Ser Glu Ala Gln Gln Tyr Leu Met Asp Asn
545                 550                 555                 560

Pro Thr Phe Ala Glu Asp Glu Glu Leu Gln Asn Met Asp Lys Glu Asp
                565                 570                 575

Ala Leu Ile Cys Phe Glu Glu His Ile Arg Ala Leu Glu Lys Glu Glu
            580                 585                 590

Glu Glu Glu Lys Gln Lys Ser Leu Leu Arg Glu Arg Arg Gln Arg
        595                 600                 605

Lys Asn Arg Glu Ser Phe Gln Ile Phe Leu Asp Glu Leu His Glu His
    610                 615                 620

Gly Gln Leu His Ser Met Ser Ser Trp Met Glu Leu Tyr Pro Thr Ile
625                 630                 635                 640

Ser Ser Asp Ile Arg Phe Thr Asn Met Leu Gly Gln Pro Gly Ser Thr
                645                 650                 655

Ala Leu Asp Leu Phe Lys Phe Tyr Val Glu Asp Leu Lys Ala Arg Tyr
            660                 665                 670

His Asp Glu Lys Lys Ile Ile Lys Asp Ile Leu Lys Asp Lys Gly Phe
        675                 680                 685

Val Val Glu Val Asn Thr Thr Phe Glu Asp Phe Val Ala Ile Ile Ser
    690                 695                 700

Ser Thr Lys Arg Ser Thr Thr Leu Asp Ala Gly Asn Ile Lys Leu Ala
705                 710                 715                 720

Phe Asn Ser Leu Leu Glu Lys Ala Glu Ala Arg Glu Arg Glu Arg Glu
                725                 730                 735

Lys Glu Glu Ala Arg Lys Met Lys Arg Lys Glu Ser Ala Phe Lys Ser
            740                 745                 750

Met Leu Lys Gln Ala Ala Pro Pro Ile Glu Leu Asp Ala Val Trp Glu
        755                 760                 765

Asp Ile Arg Glu Arg Phe Val Lys Glu Pro Ala Phe Glu Asp Ile Thr
    770                 775                 780
```

```
Leu Glu Ser Glu Arg Lys Arg Ile Phe Lys Asp Phe Met His Val Leu
785                 790                 795                 800

Glu His Glu Cys Gln His His Ser Lys Asn Lys Lys His Ser Lys
            805                 810                 815

Lys Ser Lys Lys His His Arg Lys Arg Ser Arg Ser Arg Ser Gly Ser
        820                 825                 830

Asp Ser Asp Asp Asp Ser His Ser Lys Lys Lys Arg Gln Arg Ser
    835                 840                 845

Glu Ser Arg Ser Ala Ser Glu His Ser Ser Ala Glu Ser Glu Arg
850                 855                 860

Ser Tyr Lys Lys Ser Lys Lys His Lys Lys Lys Ser Lys Lys Arg Arg
865                 870                 875                 880

His Lys Ser Asp Ser Pro Glu Ser Asp Ala Glu Arg Glu Lys Asp Lys
                885                 890                 895

Lys Glu Lys Asp Arg Glu Ser Glu Lys Asp Arg Thr Arg Gln Arg Ser
                900                 905                 910

Glu Ser Lys His Lys Ser Pro Lys Lys Lys Thr Gly Lys Asp Ser Gly
            915                 920                 925

Asn Trp Asp Thr Ser Gly Ser Glu Leu Ser Glu Gly Glu Leu Glu Lys
    930                 935                 940

Arg Arg Arg Thr Leu Leu Glu Gln Leu Asp Asp Asp Gln
945                 950                 955

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
ttgaattcaa tgggctccga cgtgcgg                                27

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 4
ttgtcgacca tgggatcctc atgctt                                26

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 5
ttgaattcaa tgggctccga cgtgcgg                                27

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 6
ttgtcgacga agacaccgtg cgtgtg                                           26

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
ttgaattcag atccaatggg ccagcag                                          27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 8
ttgtcgacga agacaccgtg cgtgtg                                           26

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 9
ctttgctggt tggctctcct cctcttct                                         28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 10
ttgatcatca tccagttgct ccaaaaggg                                        29

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 11
tgggacaaat gcctggaatg atgtcgtc                                         28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 12
cagcgatcag agtctcgttc tgcttcag                                         28
```

-continued

```
<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: 6X His tag

<400> SEQUENCE: 13

His His His His His His
  1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: 10X His tag

<400> SEQUENCE: 14

His His His His His His His His His His
  1               5                  10

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 15

Pro Pro Leu Pro
  1
```